United States Patent [19]

Broadhurst et al.

[11] Patent Number: 4,885,283

[45] Date of Patent: Dec. 5, 1989

[54] PHOSPHINIC ACID DERIVATIVES

[75] Inventors: Michael J. Broadhurst, Royston; Balraj K. Handa, Welwyn Garden City; William H. Johnson; Geoffrey Lawton, both of Hitchin; Peter J. Machin, London, all of England

[73] Assignee: Hoffmann-La Roche Inc., Nutley, N.J.

[21] Appl. No.: 126,643

[22] Filed: Dec. 1, 1987

[30] Foreign Application Priority Data

Dec. 15, 1986 [GB] United Kingdom ............... 8629876
Sep. 22, 1987 [GB] United Kingdom ............... 8722245

[51] Int. Cl.[4] ..................... A61K 31/675; C07F 9/30
[52] U.S. Cl. ......................................... 514/78; 514/86; 514/89; 514/91; 514/93; 514/92; 514/94; 514/119; 540/463; 540/487; 544/93; 544/232; 548/112; 548/413; 562/15
[58] Field of Search ............... 540/463, 487; 544/93, 544/232; 546/24; 548/112, 413, 414; 260/502.5 R, 502.5 B, 502.5 D, 502.5 E, 502.5 F; 514/78, 86, 91, 89, 93, 94, 92, 119

[56] References Cited

U.S. PATENT DOCUMENTS 4,226,610 10/1980 Takematsu et al. ......... 260/502.5 R

FOREIGN PATENT DOCUMENTS 156322 3/1985 European Pat. Off. ......... 260/502.5
152255 8/1985 European Pat. Off. ......... 260/502.5
209848 1/1987 European Pat. Off. ......... 260/502.5
210545 4/1987 European Pat. Off. ......... 260/502.5

Primary Examiner—Robert T. Bond
Attorney, Agent, or Firm—Jon S. Saxe; Bernard S. Leon; William G. Isgro

[57] ABSTRACT

The invention relates compounds of the formula

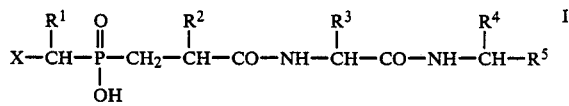

wherein $R^1$–$R^5$ and X have the significance given in the description, and their pharmaceutically acceptable salts. The compounds of formula I inhibit the enzyme collagenase and can be used in the form of medicaments for the control or prevention of degenerative joint diseases such as rheumatoid arthritis and osteoarthritis.

38 Claims, No Drawings

PHOSPHINIC ACID DERIVATIVES

BRIEF SUMMARY OF THE INVENTION

The phosphinic acid derivatives provided by the invention are compounds of the formula

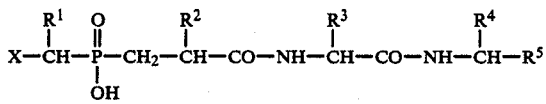

wherein
$R^1$ is hydrogen, $C_1$-$C_6$-alkyl or an aryl-($C_1$-$C_6$-alkyl);
$R^2$ is a $C_2$-$C_5$-alkyl);
$R^3$ is the side-chain of a natural α-amino acid in which any functional group present is optionally protected or any amino group present is optionally acylated or sulfonylated or any carboxyl group present is optionally amidated, with the proviso that $R^3$ does not represent hydrogen or methyl;
$R^4$ is hydrogen or methyl; or
$R^3$ and $R^4$ taken together are a group of the formula —$(CH_2)_n$— in which n is an integer from 4 to 11 inclusive;
$R^5$ is a hydrogen, $C_1$-$C_6$-alkyl, carboxyl, $C_1$-$C_6$-alkoxycarbonyl or $C_1$-$C_6$-alkylaminocarbonyl; and
X is either a cyclic imido group derived from an aliphatic or aromatic dicarboxylic acid, from an N-carboxyamino acid, from an azadicarbozylic acid or from an O-carboxyhydroxy acid, or a group of the formula

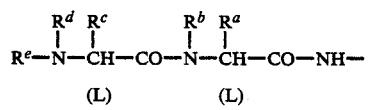

wherein $R^a$ is the side-chain of a natural α-amino acid in which any functional group present is optionally protected or any amino group present is optionally acylated or sulfonylated or any carboxyl group present is optionally amidated, $R^b$ is a hydrogen or $R^a$ and $R^b$ taken together are trimethylene, $R^c$ is the side-chain of a natural α-amino acid in which any functional group is optionally protected or any amino group present is optionally acylated or sulfonylated or any carboxyl group present is optionally amidated, $R^d$ is a hydrogen or $R^c$ and $R^d$ taken together are trimethylene and $R^e$ is a protecting group, acyl, $C_1$-$C_6$-alkyl-sulfonyl or arylsulfonyl group,
and pharmaceutically acceptable salts thereof.

In another aspect, the invention relates to pharmaceutical compositions containing compounds of formula I.

In yet another aspect, the invention relates to a method for the use of the compounds of formula I.

DETAILED DESCRIPTION OF THE INVENTION

The phosphinic acid derivatives provided by the invention are compounds of the formula

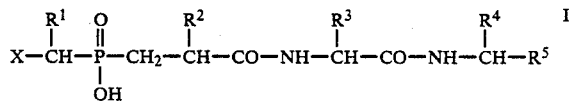

wherein
$R^1$ is hydrogen, $C_1$-$C_6$-alkyl or an aryl-($C_1$-$C_6$-alkyl);
$R^2$ is a $C_2$-$C_5$-alkyl;
$R^3$ is the side-chain of a natural α-amino acid in which any functional group present is optionally protected or any amino group present is optionally acylated or sulfonylated or any carboxyl group present is optionally amidated, with the proviso that $R^3$ does not represent hydrogen or methyl;
$R^4$ is hydrogen or methyl; or
$R^3$ and $R^4$ taken together are a group of the formula —$(CH_2)_n$— in which n is an integer from 4 to 11 inclusive;
$R^5$ is a hydrogen, $C_1$-$C_6$-alkyl, carboxyl, $C_1$-$C_6$-alkoxycarbonyl or $C_1$-$C_6$-alkylaminocarbonyl; and
X is either a cyclic imido group derived from an aliphatic or aromatic dicarboxylic acid, from an N-carboxyamino acid, from an azadicarboxylic acid or from an O-carboxyhydroxy acid, or a group of the formula

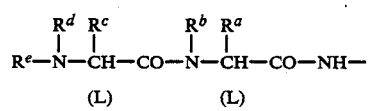

wherein $R^a$ is the side-chain of a natural α-amino acid in which any functional group present is optionally protected or any amino group present is optionally acylated or sulfonylated or any carboxyl group present is optionally amidated, $R^b$ is a hydrogen or $R^a$ and $R^b$ taken together are trimethylene, $R^c$ is the side-chain of a natural α-amino acid in which any functional group is optionally protected or any amino group present is optionally acylated or sulfonylated or any carboxyl group present is optionally amidated, $R^d$ is a hydrogen or $R^c$ and $R^d$ taken together are trimethylene and $R^e$ is a protecting group, acyl, $C_1$-$C_6$-alkyl-sulfonyl or arylsulfonyl group,
and pharmaceutically acceptable salts thereof.

As Used herein, the term "$C_1$-$C_6$-alkyl", alone or in combinations, denotes a straight-chain or branched-chain alkyl group containing from 1 to 6 carbon atoms such as methyl, ethyl, n-propyl, isopropyl, n-butyl, isobutyl, sec-butyl, tert-butyl, n-pentyl, n-hexyl or the like. The term "$C_2$-$C_5$-alkyl" denotes a straight-chain or branched-chain alkyl group containing from 2 to 5 carbon atoms. The term "$C_1$-$C_6$-alkoxy", alone or in combination, denotes an alkoxy group containing from 1 to 6 carbon atoms, examples of $C_1$-$C_6$-alkoxy groups being methoxy, ethoxy, n-propoxy, isopropoxy, n-butoxy, tert-butoxy or the like. The term "acyl" means an acyl group derived from an aliphatic carboxylic acid, for example, a $C_1$-$C_6$-alkanoic acid such as acetic acid, propionic acid, butyric acid or the like, from an aromatic carboxylic acid, for example, benzoic acid or a benzoic acid which is substituted by one or more substituents selected from $C_1$-$C_6$-alkyl, $C_1$-$C_6$-alkoxy, carboxy, halogen, trifluoromethyl, or the like or from an araliphatic carboxylic acid, for example, an aryl- ($C_1$–$C_6$-alkanoic)acid such as phenylacetic acid, or the like. The term "aryl", alone or in combinations, denotes a phenyl group which is optionally substituted with one or more substituents selected from $C_1$–$C_6$-alkyl, $C_1$–$C_6$-alkoxy, halogen, trifluoromethyl, or the like. The term "halogen" means fluorine, chlorine, bromine or iodine.

The term "side-chain of a natural α-amino acid" denotes the group R in an α-amino acid of the formula $H_2N$—CH(R)—COOH which is naturally occurring. Thus, subject to the proviso with respect to $R^3$, the side-chain can be, for example, one of the following, with the corresponding α-amino acid being indicated thereafter in parenthesis: hydrogen (glycine), methyl (alanine), isopropyl (valine), isobutyl (leucine), benzyl (phenylalanine), p-hydroxybenzyl (tyrosine), hydroxymethyl (serine), mercaptomethyl (cysteine), 1-hydroxyethyl (threonine), 2-methylthioethyl (methionine), carboxymethyl (aspartic acid), 2-carboxyethyl (glutamic acid), 3-guanidinopropyl (arginine) or 4-aminobutyl (lysine).

Any functional group present in $R^a$, $R^c$ and $R^3$ can be protected in a manner known in peptide chemistry. For example, a hydroxy group can be protected in the form of a readily cleavable ether such as the tert-butyl, benzyl or tetrahydropyranyl ether or in the form of a readily cleavable ester such as the acetate. A mercapto group can be protected, for example, by a tert-butyl, benzyl or like group. An amino group can be protected, for example, by a tert.butoxycarbonyl, benzyloxycarbonyl, formyl, trityl, trifluoroacetyl, 2-(biphenylyl)isopropoxycarbonyl or isobornyloxycarbonyl group or in the form of a phthalimido or like group. A carboxy group can be protected, for example, in the form of a readily cleavable ester such as the methyl, ethyl, tert.-butyl, benzyl or like ester.

An amino group present in $R^a$, $R^c$ and/or $R^3$ can be acylated with an acyl group as defined earlier or with an aminocarboxylic acid. Examples of such aminocarboxylic acids are α-amino acids such as the natural α-amino acids, for example, glycine, alanine, or the like. Alternatively, an amino group present in $R^a$, $R^c$ and/or $R^3$ can be sulfonylated with, for example, a $C_1$–$C_6$-alkane-sulfonic acid, for example, methanesulfonic acid or an arylsulfonic acid, for example, benzenesulfonic acid or p-toluenesulfonic acid.

A carboxyl group present in $R^a$, $R^c$ and/or $R^3$ can be amidated in a conventional manner. Thus, examples of amidated carboxyl groups are the aminocarbonyl, ($C_1$–$C_6$-alkyl)aminocarbonyl, di($C_1$–$C_6$-alkyl)aminocarbonyl or arylaminocarbonyl groups as well as a carboxyl group amidated with an aminocarboxylic acid such as a natural α-amino acid, for example, glycine, alanine or the like.

When $R^e$ in a group of formula (a) is a protecting group, this can be any amino protecting group which is known in peptide chemistry, for example, the amino protecting groups mentioned earlier.

The compounds of formula I form pharmaceutically acceptable salts with bases such as alkali metal hydroxides, for example, sodium and potassium hydroxide, alkaline earth metal hydroxides, for example, calcium hydroxide and magnesium hydroxide, ammonium hydroxide, or the like. The compounds of formula I which are basic form pharmaceutically acceptable salts with acids. As such salts there come into consideration not only salts with inorganic acids such as hydrohalic acids, for example, hydrochloric acid and hydrobromic acid, sulfuric acid, nitric acid, phosphoric acid, or the like, but also salts with organic acids such as acetic acid, tartaric acid, succinic acid, fumaric acid, maleic acid, malic acid, salicylic acid, citric acid, methanesulfonic acid, p-toluenesulfonic acid, or the like.

The compounds of formula I contain at least two asymmetric carbon atoms and can accordingly exist as optically active enantiomers, as diastereoisomers or as racemates.

In formula I above $R^1$ preferably is a hydrogen or $C_1$–$C_6$-alkyl, especially hydrogen or methyl. $R^2$ preferably is $C_3$- or $C_4$-alkyl, especially a n-propyl, isobutyl or sec.butyl group. Preferably, $R^3$ is an isobutyl group and $R^4$ is a hydrogen or $R^3$ and $R^4$ taken together are a group of the formula —$(CH_2)_n$— in which n is an integer from 5 to 9 inclusive and $R^5$ is hydrogen or $R^3$ is isobutyl, $R^4$ is methyl and $R^5$ is carboxyl or $C_1$–$C_6$-alkoxy-carbonyl group, especially a carboxyl or ethoxycarbonyl. When X is a cyclic imido group, in one preferred embodiment this is a group of the formula

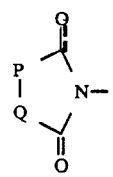 (b)

wherein P and Q taken together are a group of the formula

—CH($R^f$)—CH($R^f$)—,

—CH($R^f$)—CH($R^f$)—CH($R^f$)—,

—O—CH($R^f$)—,

—N($R^f$)—CH($R^f$)—,

—N($R^f$)—N($R^f$)—,

—N=N— or

—C($R^f$)=C($R^f$)— in which each $R^f$ is a hydrogen or $C_1$–$C_6$-alkyl, aryl, aryl-($C_1$–$C_6$-alkyl), $C_1$–$C_6$-alkanoylamino or an acylamino group in which the acyl moiety is derived from a naturally occurring α-amino acid in which the amino group is optionally protected, or P and Q taken together are an optionally substituted aromatic system in which the optional substitution comprises one or more substituents selected from $C_1$–$C_6$-alkyl, $C_1$–$C_6$-alkoxy, halogen, hydroxy, aryl-($C_1$–$C_6$-alkoxy), nitro, amino, $C_1$–$C_6$-alkanoylamino, mono($C_1$–$C_6$-alkyl)amino, di($C_1$–$C_6$-alkyl)amino and $C_1$–$C_6$-alkylsulfonylamino. In another preferred embodiment the cyclic imide X is a group of the formula

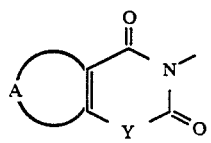 (c)

wherein A is the residue of an optionally substituted aromatic system in which the optional substitution comprises one or more substituents selected from $C_1$–$C_6$-alkyl, $C_1$–$C_6$-alkoxy, halogen, hydroxy, aryl-($C_1$–$C_6$- alkoxy), nitro, amino, $C_1$-$C_6$-alkanoylamino, mono($C_1$-$C_6$-alkyl)amino, di($C_1$-$C_6$-alkyl)amino and $C_1$-$C_6$-alkylsulfonylamino and Y is —O—, —NH— or —NR$^g$— in which R$^g$ is hydrogen or $C_1$-$C_6$-alkyl.

The optionally substituted aromatic system denoted by P and Q taken together in formula (b) can be monocyclic, for example, 1,2-phenylene or thienylene or polycyclic, for example, 1,2-naphthylene, 2,3-naphthylene, 1,8-naphthylene, 2,3-anthrylene, or the like. The symbol A in formula (c) can represent the residue of an optionally substituted monocyclic aromatic system, for example, benzene or an optionally substituted polycyclic ring system, for example, naphthalene, anthracene, or the like.

In a particularly preferred embodiment, the cyclic imide group X is a group of formula (b) wherein P and Q taken together are a group of the formula —C(R$^f$)=C(R$^f$)— in which one R$^f$ is aryl, especially phenyl, and the other R$^f$ is hydrogen or aryl, especially phenyl. In another particularly preferred embodiment the cyclic imido group X is a group of formula (b) wherein P and Q taken together are 1,2-phenylene or 2,3-naphthylene which is optionally substituted by one or more substituents selected from $C_1$-$C_6$-alkoxy, halogen, hydroxy, amino and $C_1$-$C_6$-alkanoylamino. In yet another particularly preferred embodiment the cyclic imide group X is a group of formula (b) wherein P and Q taken together are a 1,8-naphthylene group which is optionally substituted by one or more substituents selected from $C_1$-$C_6$-alkoxy, halogen, hydroxy, amino and $C_1$-$C_6$-alkanoylamino. In a further particularly preferred embodiment, the cyclic imido group X is a group of a formula (c) in which A is the residue of a benzene ring and Y is —NR$^g$—.

When X is a group of formula (a) above, preferably R$^a$ is the side-chain of a natural α-amino acid in which any functional group present is optionally protected or any amino group present is optionally acylated or sulfonylated or any carboxyl group present is optionally amidated, especially an isobutyl group, and R$^b$ is a hydrogen, R$^c$ and R$^d$ taken together are trimethylene and R$^e$ is a protecting group, especially a benzyloxycarbonyl group, or an acyl group, especially acetyl.

Particularly preferred compounds of formula I hereinbefore are:

[(3-aminophthalimido)methyl][(RS)-4-methyl-2-[[(S)-3-methyl-1-(methylcarbamoyl)butyl]carbamoyl]pentyl]phosphinic acid,

[(RS)-4-methyl-2-[[(S)-3-methyl-1-(methylcarbamoyl)butyl]carbamoyl]pentyl](1,8-naphthalenedicarboximidomethyl)phosphinic acid,

[(R or S)-4-methyl-2-[[(R or S)-2-oxo-3-azacyclotridecyl]carbamoyl]pentyl](1,8-naphthalenedicarboximidomethyl)phosphinic acid, N-[N-[(R or S)-2-[[[[N-[1-(benzyloxy)carbonyl]-L-prolyl]-L-leucyl]amino]methyl]hydroxyphosphinyl]-methyl]-4-methylvaleryl]-L-leucyl]-L-alanine, and

[[1,4-dihydro-2,4-dioxo-3(2H)-quinazolinyl]methyl]-[[(R or S)-4-methyl-2-[[(R or S)-2-oxo-3-azacyclotridecyl]-carbamoyl]pentyl]phosphinic acid.

According to the process provided by the invention, the compounds of formula I above and their pharmaceutically acceptable salts can be prepared by treating a compound of the formula

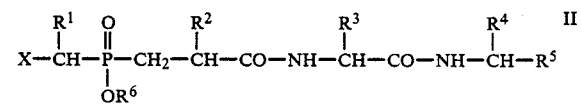

wherein $R^1$, $R^2$, $R^3$, $R^4$, $R^5$ and X have the significance given above and $R^6$ is a $C_1$-$C_6$-alkyl, with an acid or with a halotrimethylsilane, if desired functionally modifying a reactive substituent present on a cyclic imide group denoted by X in a compound of formula I obtained and, also if desired, converting a compound of formula I obtained into a pharmaceutically acceptable salt.

The treatment of a compound of formula II, preferably one in which $R^6$ is methyl or ethyl, with an acid or with a halotrimethylsilane can be carried out in a known manner. Thus, for example, a compound of formula II can be treated with hydrogen bromide in acetic acid at about room temperature or with trifluoroacetic acid in an inert organic solvent, for example, a halogenated hydrocarbon such as dichloromethane or the like at about room temperature. Again, for example, a compound of formula II can be treated with a halotrialkylsilane, preferably bromotrimethylsilane, in an inert organic solvent, for example, a halogenated hydrocarbon such as dichloromethane or the like at about room temperature.

A reactive substituent which is present on a cyclic imido group denoted by X in a compound of formula I can be functionally modified if desired. Thus, for example, a nitro group can be reduced to an amino group in a known manner, for example, by hydrogenation in the presence of a catalyst such as a palladium catalyst. Again, for example, an aryl-($C_1$-$C_6$-alkoxy) group such as benzyloxy can be converted into a hydroxy group in a known manner, for example, by hydrogenation in the presence of a catalyst such as a palladium catalyst. Further, for example, an activated aromatic hydrogen atom can be replaced by a halogen atom by halogenation in a known manner.

A compound of formula I obtained can be converted into a pharmaceutically acceptable salt in accordance with known methods. Thus, a compound of formula I can be converted into a pharmaceutically acceptable salt by treatment with a base such as one of the bases mentioned earlier. A compound of formula I which is basic can be converted into a pharmaceutically acceptable acid addition salt by treatment with an acid such as one of the acids mentioned earlier.

The compounds of formula II which are used as starting materials in the process provided by the invention also form part of the invention.

The compounds of formula II can be prepared, for example, by condensing a compound of the formula

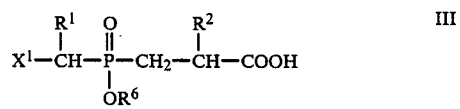

wherein $R^1$, $R^2$ and $R^6$ have the significance given earlier and $X^1$ is either a cyclic imido group as defined earlier or a group of the formula

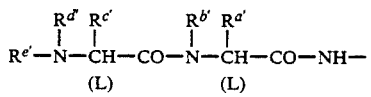 (a')

wherein $R^{a'}$ is the side-chain of a natural α-amino acid in which any functional group present is protected and $R^{b'}$ is hydrogen or $R^{a'}$ and $R^{b'}$ taken together are trimethylene, $R^{c'}$ is the side-chain of a natural α-amino acid in which any functional group present is protected and $R^{d'}$ is hydrogen or $R^{c'}$ and $R^{d'}$ taken together are trimethylene and $R^{e'}$ is a protecting group,
with a compound of the formula

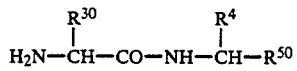 IV wherein $R^{30}$ is the side-chain of a natural α-amino acid in which any functional group is protected and $R^4$ has the significance given earlier or $R^{30}$ and $R^4$ taken together are a group of the formula $-(CH_2)_n-$ in which n has the significance given earlier and $R^{50}$ has the same significance as $R^5$ earlier except that any carboxyl group which is present is protected,
to give a compound of the formula

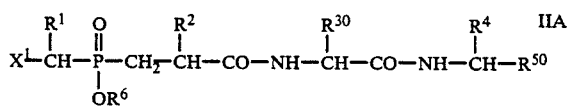 IIA wherein $R^1$, $R^2$, $R^4$, $R^6$, $R^{30}$, $R^{50}$ and $X^1$ have the significance given earlier,
and, where required, converting any protected carboxyl group $R^{50}$ into a carboxyl group, if desired cleaving off the protecting group $R^{e'}$ and appropriately acylating or sulfonylating the resulting compound, if desired cleaving off any protecting group present on $R^{a'}$ and/or $R^{c'}$ and/or $R^{30}$ and, also if desired, appropriately acylating or sulfonylating any amino group obtained or amidating any carboxyl group obtained.

The condensation of a compound of formula III with a compound of formula IV can be carried out in a manner known in peptide chemistry. Thus, for example, the condensation can be carried out according to the acid halide, acid anhydride, activated amide, mixed carbonic anhydride or activated ester method. In a preferred procedure, the condensation is carried out according to the activated ester method, particularly using hydroxybenzotriazole in the presence of a condensation agent such as N,N'-dicyclohexylcarbodiimide.

The subsequent steps which can be carried out on a condensation product of formula IIA are known in peptide chemistry and, accordingly, the methods used and the sequence in which the steps can be carried out will be evident and familiar to any person of ordinary skill in the art.

The compounds of formula III hereinbefore can be prepared by reacting a compound of the formula

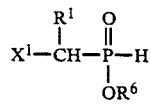 V wherein $R^1$, $R^6$ and $X^1$ have the significance given earlier,
with a compound of the formula

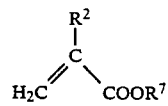 VI wherein $R^2$ has the significance given earlier and $R^7$ is a protecting group, for example, benzyl, which is selectively cleavable in the presence of $R^6$,
and cleaving off the protecting group $R^7$ from the resulting compound of the formula

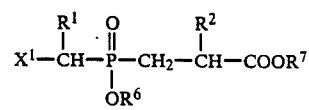 VII wherein $R^1$, $R^2$, $R^6$, $R^7$ and $X^1$ have the significance given earlier.

The reaction of a compound of formula V with a compound of formula VI and the cleavage of the protecting group $R^7$ from the resulting compound of formula VII can be carried out according to methods generally known.

The compounds of formula III in which $X^1$ is a cyclic imido group as hereinbefore defined can also be prepared by reacting a compound of the formula

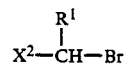 VIII wherein $R^1$ has the significance given earlier and $X^2$ is a cyclic imido group as hereinbefore defined,
with a compound of the formula

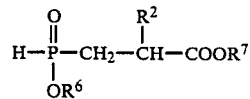 IX wherein $R^2$, $R^6$ and $R^7$ have the significance given earlier,
and cleaving off the protecting group $R^7$ from the resulting compound of the formula

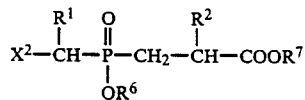 X wherein $R^1$, $R^2$, $R^6$, $R^7$ and $X^2$ have the significance given earlier.

The reaction of a compound of formula VIII with a compound of formula IX and the cleavage of the protecting group $R^7$ from the resulting compound of formula X can be carried out according to generally known methods.

A further method for the preparation of the compounds of formula II hereinbefore comprises introducing a cyclic imido group or a group of the formula

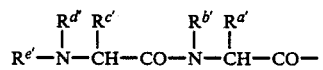
(d)

wherein $R^{a'}$, $R^{b'}$, $R^{c'}$, $R^{d'}$ and $R^{e'}$ have the significance given earlier,
into a compound of the formula

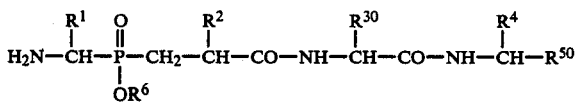

wherein $R^1$, $R^2$, $R^4$, $R^6$, $R^{30}$ and $R^{50}$ have the significance given earlier,
and, where required, converting any protected carboxyl group denoted by $R^{50}$ into a carboxyl group, if desired, cleaving off the protecting group $R^{e'}$ and appropriately acylating or sulfonylating the resulting compound, if desired cleaving off any protecting group present on $R^{a'}$ and/or $R^{c'}$ and/or $R^{30}$ and, also if desired, appropriately acylating or sulfonylating any amino group obtained or amidating any carboxyl group obtained.

The introduction of a cyclic imido group or a group of formula (d) into a compound of formula XI can be carried out in a manner known in peptide chemistry. For example, a cyclic imido group can be introduced by reacting a compound of formula XI with an anhydride derived from an aliphatic or aromatic dicarboxylic acid, an N-carboxyamino acid, an azadicarboxylic acid or an O-carboxyhydroxy acid in accordance with known methods. A group of formula (d) can be introduced by condensing a compound of formula XI with an appropriate dipeptide or, preferably, in two stages, by condensing a compound of formula XI with an appropriately protected natural α-amino acid, suitably deprotecting the condensation product and then condensing the deprotected compound obtained with a further appropriately protected natural α-amino acid. It will, of course, be appreciated that in this preferred procedure the protected natural α-amino acids used can be the same or different.

The subsequent steps which can be carried out on the product obtained after introduction of a cyclic imido group or a group of formula (d) are well known in peptide chemistry and, accordingly, the methods used and the sequence in which the steps can be carried out will be familiar to any person skilled in the art.

The compounds of formula XI can be prepared by treating a compound of formula IIA in which $X^1$ represents a phthalimido group with hydrazine in a known manner, for example, using hydrazine hydrate in an inert organic solvent such as an alkanol, for example, methanol, ethanol or the like, at about room temperature.

The compounds of formula XI can also be prepared by reacting a compound of the formula

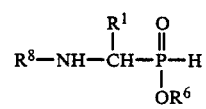
XII wherein $R^1$ and $R^6$ have the significance given earlier and $R^8$ is a protecting group, (XI)

with a compound of formula VI hereinbefore, cleaving off the protecting group $R^7$ from the resulting compound of the formula

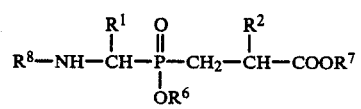
XIII wherein $R^1$, $R^2$, $R^6$ and $R^8$ have the significance given earlier,
condensing the resulting compound of the formula

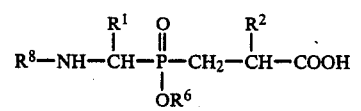
XIV wherein $R^1$, $R^2$, $R^6$ and $R^8$ have the significance given earlier,
with a compound of formula IV hereinbefore and cleaving off the protecting group $R^8$ and converting any protected carboxyl group $R^{50}$ into a carboxyl group in the thus-obtained compound of the formula

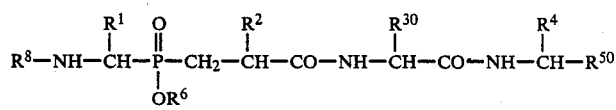
XV wherein $R^1$, $R^2$, $R^4$, $R^6$, $R^8$, $R^{30}$ and $R^{50}$ have the significance given earlier.

This latter procedure for the preparation of the compounds of formula XI can also be carried out according to methods generally known.

A further method for the preparation of compounds of formula III in which $X^1$ is a group of formula (b) wherein P and Q taken together are a group of the formula —N(R$^f$)—CH(R$^g$)— comprises treating a compound of formula VII in which $X^1$ is phthalimido with hydrazine, condensing the resulting compound of the formula

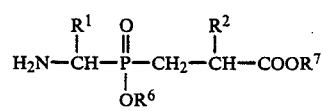
XVI wherein $R^1$, $R^2$, $R^6$ and $R^7$ have the significance given earlier,
with an appropriately protected amino acid, treating the condensation product of the formula

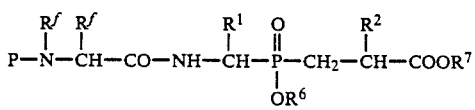

wherein $R^1$, $R^2$, $R^6$, $R^7$ and $R^f$ have the significance given earlier and P is a protecting group,
removing the protecting group P, reacting the resulting compound of the formula

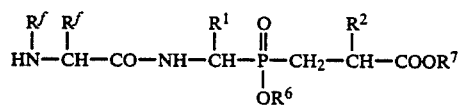

wherein $R^1$, $R^2$, $R^6$, $R^7$ and $R^f$ have the significance given earlier,
with phosgene and cleaving off the protecting group $R^7$ from the resulting compound of the formula

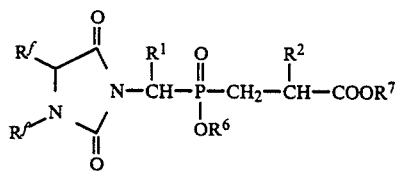

wherein $R^1$, $R^2$, $R^6$, $R^7$ and $R^f$ have the significance given earlier.

This procedure for the preparation of a compound of formula III in which $X^1$ is a group of formula (b) wherein P and Q taken together are a group of the formula —N(R^f)—CH(R^f)— can be carried out according to known methods.

The compounds of formulas IV, V, VI, VIII, IX and XII hereinbefore are known compounds or analogues of known compounds which can be prepared in a similar manner to the known compounds or as described in the Examples hereinafter.

The compounds of formula I hereinbefore and their pharmaceutically acceptable salts inhibit the enzyme collagenase and can be used in the control or prevention of degenerative joint diseases such as rheumatoid arthritis and osteoarthritis.

The in vitro inhibitory activity of the compounds of formula I can be demonstrated against collagenase obtained from a culture of human synovial fibroblasts according to the method of Dayer et al., Proc. Natl. Acad. Sci. USA (1976), 73, 945, following activation of the procollagenase in the conditioned medium by treatment with trypsin. Collagenase activity was measured using $^{14}C$-acetylated collagen type I from rat tail tendons as the substrate and employing the microtitre plate assay method of Johnson-Wint, B. Anal. Biochem. (1980), 104, 175. The $IC_{50}$ is that concentration of a compound of formula I of the invention in the enzyme digestion which reduces substrate cleavage and solubilization to 50% of that achieved by the enzyme alone.

The results obtained in the foregoing test with representative compounds of this invention are compiled in the Table I hereinafter:

TABLE I

| Compound of formula I | $IC_{50}$ |
|---|---|
| A | $5.6 \times 10^{-8}$ |
| B | $6 \times 10^{-7}$ |

TABLE I-continued

| Compound of formula I | $IC_{50}$ |
|---|---|
| C | $1.6 \times 10^{-7}$ |
| D | $1.1 \times 10^{-7}$ |
| E | $2.2 \times 10^{-7}$ |

Compound A: N—[N—[(R or S)-2-[[[[[N—[1-(Benzyloxy)carbonyl]-L-prolyl]-L-leucyl]amino]methyl]hydroxyphosphinyl]methyl]-4-methylvaleryl]-L-leucyl]-L-alanine.
Compound B: [(3-Aminophthalimido)methyl][(RS)-4-methyl-2-[[(S)-3-methyl-1-(methylcarbamoyl)butyl]carbamoyl]pentyl]phosphinic acid.
Compound C: [(RS)-4-Methyl-2-[[(S)-3-methyl-1-(methylcarbamoyl)butyl]carbamoyl]pentyl](1,8-naphthalenedicarboximidomethyl)phoshinic acid.
Compound D: [(R or S)-4-Methyl-2-[[(R or S)-2-oxo-3-azacyclotridecyl]carbamoyl]pentyl](1,8-naphthalenedicarboximidomethyl)phosphinic acid.
Compound E: [[1,4-Dihydro-2,4-dioxo-3(2H)-quinazolinyl]-methyl][[(R or S)-4-methyl-2-[[(R or S)-2-oxo-3-azacyclotridecyl]carbamoyl]pentyl]phosphinic acid.

The in vivo activity of the compounds of formula I can be demonstrated using the following test procedure. Groups of female rats received an intradermal injection into the shaved backs of $10 \times 0.1$ ml of an emulsion of type II collagen/Freund's incomplete adjuvant. Ten days later the test compound was administered twice daily at a dosage of 20 mg kg$^{-1}$ via indwelling jugular vein catheters; dosing was continued for 12 days. Groups of rats which received the intradermal injection, but which were not treated with test compounds, served as the control. The incidence of hind paw inflammation was assessed visually at intervals throughout the test and was expressed as the proportion of the group showing signs of erythema and/or swelling. Radiological change in the ankle region of the hind paws was assessed at the termination of the test and was quantified using an arbitrary scale of from 0=normal to 6=severe change, results being expressed as group means. Statistical analysis was performed using the Mann-Whitney "U" test.

TABLE II

| | Inflammation day 4 | Radiological scores | |
|---|---|---|---|
| | | Talus | Tarsus |
| Control | 8/11 | $2.28 \pm 0.53$ | $1.75 \pm 0.45$ |
| Compound D | 3/12 | $0.86 \pm 0.34$ | $0.64 \pm 0.37$ |

Compound D given in this Table is compound D named in connection with Table I earlier.

The compounds of formula I and their pharmaceutically acceptable salts can be used as medicaments in the form of pharmaceutical preparations which contain them in association with a compatible pharmaceutical carrier material. This carrier material can be an organic or inorganic carrier material which is suitable for enteral or parenteral administration such as water, lactose, starch, magnesium stearate, talc, gum arabic, gelatine, polyalkylene glycols, petroleum jelly or the like. The pharmaceutical preparations can be made up in a solid form, for example, as tablets, powders, dragees, suppositories, capsules or the like, or in a liquid form, for example, as solutions, emulsions, suspensions or the like.

If necessary, the pharmaceutical preparations can be subjected to conventional pharmaceutical operations such as sterilization and the like and they can also contain conventional pharmaceutical adjuvants such as preserving agents, stabilizing agents, wetting agents, salts for varying the osmotic pressure or the like. The present pharmaceutical preparations may also contain other therapeutically active substances.

The pharmaceutical preparations can be prepared by mixing a compound of formula I or a pharmaceutically acceptable salt thereof and, if desired, one or more other therapeutically active substances with a therapeutically inert carrier material and bringing the mixture obtained into a galenical administration form.

The compounds of formula I and their pharmaceutically acceptable salts may be administered to adults in a dosage range of from about 5 mg to 30 mg, preferably about 10 mg to 15 mg, per day. It will, of course, be appreciated that this dosage range is given by way of example only and that it can be varied upwards or downwards depending on factors such as the potency of the particular compound or salt to be administered, the particular condition to be treated and the individual requirements of the patient as determined by the attending physician.

The following Examples further illustrate the invention. In these Examples, the structures of the compounds obtained were confirmed by nuclear magnetic resonance data, mass spectra and/or microanalyses.

EXAMPLE 1

(A) THE PREPARATION OF THE STARTING MATERIAL (i) A mixture of 7.98 g (0.12 mol) of crystalline phosphinic acid and 15.96 g (0.15 mol) of trimethyl orthoformate was stirred at room temperature under nitrogen for 1 hour. The resulting solution was then added dropwise to a stirred mixture of 7.98 g (0.037 mol) of benzyl isobutylacrylate and 3.14 g (0.027 mol) of 1,1,3,3-tetramethylguanidine at such a rate that the temperature was maintained at 0°-8° C. by means of an external cooling bath. After completion of the addition the cooling bath was removed, the mixture was allowed to come to room temperature and was then stirred for 2 hours. The mixture was diluted with 250 ml of dichloromethane and the solution was washed with 200 ml of water and 200 ml of 10% sulfuric acid. The combined aqueous extracts were extracted with two 50 ml portions of dichloromethane and the combined dichloromethane extracts were washed with sodium chloride solution, dried over anhydrous sodium sulfate and evaporated to yield 12.62 g of a colorless oil containing benzyl 2-[(methoxyphosphinyl)methyl]-4-methylvalerate.

(ii) Six (6.0) g of crude benzyl 2-[(methoxyphosphinyl)-methyl]-4-methylvalerate were dissolved in 30 ml of dichloromethane and the solution was cooled in an ice-bath while stirring under nitrogen. Nine (9) ml of bis(trimethyl-silyl)acetamide and 2.6 g of diisopropylethylamine were added, the mixture was stirred for 5 minutes and then 4.8 g of N-bromomethylphthalimide were added. The cooling bath was removed, the mixture was left to come to room temperature, stirred for 5 hours and then an additional 20 ml of dichloromethane were added. The solution was washed with 50 ml of 10% sulfuric acid and 50 ml of sodium chloride solution, dried over anhydrous sodium sulfate and evaporated to give 8.6 g of a yellow oil which was purified by flash chromatography on silica gel using ethyl acetate/n-hexane (3:1) for the elution. There were obtained 4.22 g of benzyl 2(RS)-[[(RS)-(methoxy)(phthalimidomethyl)phosphinyl]methyl]-4-methylvalerate in the form of a colorless oil.

(iii) 4.5 g of benzyl 2(RS)-[[(RS)-(methoxy)(phthalimidomethyl)phosphinyl]methyl]-4-methylvalerate were dissolved in 200 ml of methanol and the solution was hydrogenated over 1.9 g of 10% palladium-on-charcoal for 3.5 hours. After filtration and evaporation of the filtrate there were obtained 3.0 g of a white foam containing 2(RS)-[[(RS)-(methoxy)(phthalimidomethyl)phosphinyl]methyl]-4-methylvaleric acid.

(iv) 3.0 g of 2(RS)-[[(RS)-(methoxy)(phthalimidomethyl)phosphinyl]methyl]-4-methylvaleric acid were dissolved in 50 ml of tetrahydrofuran and 1.65 g of L-leucine N-methylamide and 2.2 g of hydroxybenzotriazole were added while stirring. After all of the solids had dissolved, 2.02 g of N,N'-dicyclohexylcarbodiimide were added and the mixture was stirred at room temperature overnight. The tetrahydrofuran was removed by evaporation, the residue was triturated with 100 ml of ethyl acetate and the mixture was filtered in order to remove dicyclohexylurea. The filtrate was washed twice with 50 ml of saturated sodium hydrogen carbonate solution each time, dried over anhydrous sodium sulfate and evaporated to give a yellow gum. This gum was purified by flash chromatography on silica gel using 5% methanol in ethyl acetate for the elution. There were obtained 3.32 g of [(RS)-4-methyl-2-[[(S)-3-methyl-1-(methylcarbamoyl)butyl]carbamoyl]-4-methylpentyl](phthalimidomethyl)phosphinic acid methyl ester in the form of a white foam.

(B) THE PROCESS 123 mg of [(RS)-4-methyl-2-[[(S)-3-methyl-1-(methylcarbamoyl)butyl]carbamoyl]-4-methylpentyl](phthalimidomethyl)phosphinic acid methyl ester were dissolved in a mixture of 3 ml of acetic acid and 3 ml of 48% hydrogen bromide in acetic acid and the mixture was left to stand at room temperature for 18 hours. The solvent was removed by evaporation, the residue was dissolved in a mixture of 10 ml of toluene and 5 ml of acetone and the solution was evaporated. This procedure was repeated twice and the residue was then dissolved in a mixture of 5 ml of dichloromethane and 3 ml of acetone and the solution was evaporated. After drying under a high vacuum (0.1 mmHg), there were obtained 115 mg of [(RS)-4-methyl-2-[[(S)-3-methyl-1-(methylcarbamoyl)butyl]carbamoyl]pentyl](phthalimidomethyl)phosphinic acid in the form of an off-white foam.

EXAMPLE 2

(A) THE PREPARATION OF THE STARTING MATERIAL (i) 2.5 g of [(RS)-4-methyl-2-[[(S)-3-methyl-1-(methylcarbamoyl)butyl]carbamoyl]-4-methylpentyl](phthalimidomethyl)phosphinic acid methyl ester, prepared as described in Example 1(A)(v), were dissolved in 30 ml of a 0.33M solution of hydrazine hydrate in methanol. The mixture was stirred at room temperature for 18 hours and was then evaporated. The residue was suspended in 50 ml of dichloromethane and 0.7 g of glacial acetic acid was added. After standing at room temperature for 1 hour the precipitated phthalhydrazide was removed by filtration and the filtrate was evaporated to give a colorless gum which was purified by chromatography on silica gel using chloroform/methanol/acetic acid/water (60:18:2:3) for the elution. There were obtained 1.84 g of (aminomethyl)[(RS)-4-methyl-2-[[(S)-3-methyl-1-(methylcarbamoyl)butyl]carbamoyl]pentyl]phosphinic acid methyl ester acetate in the form of a colorless gum.

(ii) 0.4 g of (aminomethyl)[(RS)-4-methyl-2-[[(S)-3-methyl-1-(methylcarbamoyl)butyl]carbamoyl]pentyl]phosphinic acid methyl ester acetate was dissolved in 15 ml of dichloromethane and 0.12 g of maleic anhydride and 0.12 g of triethylamine were added. The mixture was stirred at room temperature for 1 hour and then diluted with 20 ml of dichloromethane. The solution was washed with 5 ml of 10% sulfuric acid, dried over anhydrous sodium sulfate and evaporated to give 0.31 g of a colorless gum which was dissolved in 5 ml of dimethylformamide. 0.135 g of hydroxybenzotriazole and 0.15 g of N,N'-dicyclohexylcarbodiimide were added to the dimethylformamide solution and the mixture was stirred at room temperature overnight. The dimethylformamide was removed by evaporation, the residue was triturated with 30 ml of ethyl acetate and the mixture was filtered in order to remove dicyclohexylurea. The filtrate was washed twice with 30 ml of saturated sodium hydrogen carbonate solution each time, dried over anhydrous sodium sulfate and evaporated to give a colorless gum. This gum was purified by flash chromatography on silica gel using 10% methanol in dichloromethane for the elution. There was obtained 0.155 g of (maleimido)[(RS)-4-methyl-2-[[(S)-3-methyl-1-(methylcarbamoyl)butyl]carbamoyl]pentyl]phosphinic acid methyl ester in the form of a colorless gum.

(B) THE PROCESS 60 mg of (maleimido)[(RS)-4-methyl-2-[[(S)-3-methyl-1-(methylcarbamoyl)butyl]carbamoyl]pentyl]phosphinic acid methyl ester were dissolved in 5 ml of dichloromethane and 0.5 ml of bromotrimethylsilane were added. After stirring at room temperature for 1.5 hours the solvent was removed by evaporation and the residue was re-evaporated twice with 20 ml of acetone each time. The residue was then dissolved in 5 ml of acetone and 0.25 ml of water. After standing at room temperature for 15 minutes, the solvent was removed by evaporation. The residue was dissolved in 10 ml of dichloromethane and 50 mg of triethylamine were added. After 2 hours, the solution was washed with 10 ml of sodium chloride solution and evaporated to give 75 mg of (maleimidomethyl)[(RS)-4-methyl-2-[[(S)-3-methyl-1-(methylcarbamoyl)butyl]carbamoyl]pentyl]phosphinic acid triethylamine salt in the form of a white foam.

EXAMPLE 3

(A) THE PREPARATION OF THE STARTING MATERIAL 0.36 g of (aminomethyl)[(RS)-4-methyl-2-[[(S)-3-methyl-1-(methylcarbamoyl)butyl]carbamoyl]pentyl]phosphinic acid methyl ester acetate, prepared as described in Example 2(A)(i), was dissolved in 10 ml of dichloromethane and 0.17 g of succinic anhydride and 0.17 g of triethylamine were added. After stirring at room temperature for 2 hours, 0.2 g of hydroxybenzotriazole and 0.2 g of N,N'-dicyclohexylcarbodiimide were added. The mixture was stirred at room temperature for 18 hours and then filtered in order to remove dicyclohexylurea. The filtrate was washed twice with 15 ml of saturated sodium hydrogen carbonate solution each time. After drying over anhydrous sodium sulfate the solvent was removed by evaporation to give a colorless gum. This gum was purified by flash chromatography on silica gel using ethyl acetate/methanol (8:1) for the elution. There was obtained 0.23 g of [(RS)-4-methyl-2-[[(S)-3-methyl-1-(methylcarbamoyl)butyl]carbamoyl]pentyl](succinimidomethyl)phosphinic acid methyl ester in the form of a white foam.

(B) THE PROCESS 60 mg of [(RS)-4-methyl-2-[[(S)-3-methyl-1-(methylcarbamoyl)butyl]carbamoyl]pentyl](succinimidomethyl)phosphinic acid methyl ester were dissolved in 5 ml of dichloromethane, 0.5 ml of bromotrimethylsilane was added and the mixture was stirred at room temperature for 1.5 hours. The solvent was removed by evaporation and the residue was then re-evaporated twice with 20 ml of acetone each time. The residue was dissolved in 5 ml of acetone and 0.25 ml of water. After standing at room temperature for 15 minutes, the solvent was removed by evaporation and the residue was dissolved in 20 ml of acetone/dichloromethane (1:2). The solution was then evaporated to give 56 mg of [(RS)-4-methyl-2-[[(S)-3-methyl-1-(methylcarbamoyl)butyl]carbamoyl]pentyl](succinimidomethyl)phosphinic acid in the form of a white foam.

EXAMPLE 4

(A) THE PREPARATION OF THE STARTING MATERIAL

In a manner analogous to that described in Example 3(A), from 0.7 g of (aminomethyl)[(RS)-4-methyl-2-[[(S)-3-methyl-1-(methylcarbamoyl)butyl]carbamoyl]pentyl]phosphinic acid methyl ester acetate and 0.29 g of phenylmaleic anhydride, there was obtained 0.21 g of [(RS)-4-methyl-2-[[(S)-3-methyl-1-(methylcarbamoyl)butyl]carbamoyl]pentyl][(2-phenylmaleimido)methyl]phosphinic acid methyl ester in the form of a pale yellow foam.

(B) THE PROCESS 0.1 g of [(RS)-4-methyl-2-[[(S)-3-methyl-1-(methylcarbamoyl)butyl]carbamoyl]pentyl][(2-phenylmaleimido)methyl]phosphinic acid methyl ester was dissolved in 1 ml of dichloromethane and 2 ml of trifluoroacetic acid were added. The mixture was stirred at room temperature for 2 hours and the solvent was then removed by evaporation. The residue was taken up in 30 ml of acetone/dichloromethane (1:1) and the solution was evaporated to give 95 mg of [(RS)-4-methyl-2-[[(S)-3-methyl-1-(methylcarbamoyl)butyl]carbamoyl]pentyl][(2-phenylmaleimido)methyl]phosphinic acid in the form of a tan colored foam.

EXAMPLE 5

(A) THE PREPARATION OF THE STARTING MATERIAL

In a manner analogous to that described in Example 3 (A), from 0.4 g of (aminomethyl)[(RS)-4-methyl-2-[[(S)-3-methyl-1-(methylcarbamoyl)butyl]carbamoyl]pentyl]phosphinic acid methyl ester acetate and 0.178 g of 3-methoxy-phthalic anhydride, there was obtained 0.1 g of [(3-methoxyphthalimido)methyl][(RS)-4-methyl-2-[[(S)-3-methyl-1-(methylcarbamoyl)butyl]carbamoyl]pentyl]phosphinic acid methyl ester in the form of a colorless foam.

(B) THE PROCESS 0.1 g of [(3-methoxyphthalimido)methyl][(RS)-4-methyl-2-[[(S)-3-methyl-1-(methylcarbamoyl)butyl]carbamoyl]pentyl]phosphinic acid methyl ester was treated according to the procedure described in of Example 3(B) to give 95 mg of [(3-methoxyphthalimido)methyl][(RS)-4-methyl-2-[[(S)-3-methyl-1-(methylcarbamoyl)butyl]carbamoyl]pentyl]phosphinic acid in the form of a white foam.

EXAMPLE 6

(A) THE PREPARATION OF THE STARTING MATERIAL

In a manner analogous to that described in Example 3(A), from 0.45 g of (aminomethyl)[(RS)-4-methyl-2-[[(S)-3-methyl-1-(methylcarbamoyl)butyl]carbamoyl]pentyl]phosphinic acid methyl ester acetate and 0.185 g of 4-methoxyphthalic anhydride, there was obtained 0.274 g of [(4-methoxyphthalimido)methyl][(RS)-4-methyl-2-[[(S)-3-methyl-1-(methylcarbamoyl)butyl]carbamoyl]pentyl]phosphinic acid methyl ester in the form of colorless foam.

(B) THE PROCESS 0.1 g of [(4-methoxyphthalimido)methyl][(RS)-4-methyl-2-[[(S)-3-methyl-1-(methylcarbamoyl)butyl]carbamoyl]pentyl]phosphinic acid methyl ester was treated according to the procedure described in Example 3(B) to give 94 mg of [(4-methoxyphthalimido)methyl][(RS)-4-methyl-2-[[(S)-3-methyl-1-(methylcarbamoyl)butyl]carbamoyl]pentyl]phosphinic acid in the form of a colorless foam.

EXAMPLE 7

(A) THE PREPARATION OF THE STARTING MATERIAL

In a manner analogous to that described in Example 3(A), from 0.285 g of (aminomethyl)[(RS)-4-methyl-2-[[(S)-3-methyl-1-(methylcarbamoyl)butyl]carbamoyl]pentyl]phosphinic acid methyl ester acetate and 0.15 g of 1,8-naphthalic anhydride, there was obtained 0.195 g of [(RS)-4-methyl-2-[[(S)-3-methyl-1-(methylcarbamoyl)butyl]carbamoyl]pentyl](1,8-naphthalendicarboximidomethyl)phosphinic acid methyl ester in the form of a pale yellow foam.

(B) THE PROCESS 0.16 g of [(RS)-4-methyl-2-[[(S)-3-methyl-1-(methylcarbamoyl)butyl]carbamoyl]pentyl](1,8-naphthalendicarboximidomethyl)phosphinic acid methyl ester was treated according to the procedure described in Example 3(B) to give 155 mg of [(RS)-4-methyl-2-[[(S)-3-methyl-1-(methylcarbamoyl)butyl]carbamoyl]pentyl](1,8-naphthalendicarboximidomethyl)phosphinic acid in the form of a pale yellow foam.

EXAMPLE 8

(A) THE PREPARATION OF THE STARTING MATERIAL

In a manner analogous to that described in Example 3(A), from 0.41 g of (aminomethyl)[(RS)-4-methyl-2-[[(S)-3-methyl-1-(methylcarbamoyl)butyl]carbamoyl]pentyl]phosphinic acid methyl ester acetate and 0.21 g of 3-methyl-6-methoxyphthalic anhydride there was obtained 0.245 g of [(3-methoxy-6-methylphthalimido)methyl][(RS)-4-methyl-2-[[(S)-3-methyl-1-(methylcarbamoyl)butyl]carbamoyl]pentyl]phosphinic acid methyl ester in the form of a white foam.

(B) THE PROCESS 0.1 g of [(3-methoxy-6-methylphthalimido)methyl][(RS)-4-methyl-2-[[(S)-3-methyl-1-(methylcarbamoyl)butyl]carbamoyl]pentyl]phosphinic acid methyl ester was treated according to the procedure described in Example 3(B) to give 95 mg of [(3-methoxy-6-methylphthalimido)methyl][(RS)-4-methyl-2-[[(S)-3-methyl-1-(methylcarbamoyl)butyl]carbamoyl]pentyl]phosphinic acid in the form of a white foam.

EXAMPLE 9

(A) THE PREPARATION OF THE STARTING MATERIAL (i) A solution of 0.53 g of N-[(benzyloxy)carbonyl]-L-leucine in 10 ml of dry tetrahydrofuran was cooled to −30° C. and there was then added 0.23 g of N-ethylmorpholine followed by 0.27 g of isobutyl chloroformate. After stirring at −30° C. for 5 minutes a solution of 0.6 g of (aminomethyl)[(RS)-4-methyl-2-[[(S)-3-methyl-1-(methylcarbamoyl)butyl]carbamoyl]pentyl]phosphinic acid methyl ester, prepared as described in Example 2(A)(i), and 0.23 g of N-ethylmorpholine were added. The mixture was left to come to room temperature and was stirred at this temperature for 3.5 hours. The mixture was then diluted with 50 ml of dichloromethane, washed with 20 ml of 10% sulfuric acid, 20 ml of sodium chloride solution and 20 ml of saturated sodium hydrogen carbonate solution, dried over anhydrous sodium sulfate and evaporated to give a colorless gum. This gum was purified by flash chromatography on silica gel using 10% methanol in ethyl acetate for the elution to give 0.645 g of benzyl[(S)-1-[[[methoxy[(RS)-4-methyl-2-[[(S)-3-methyl-1-(methylcarbamoyl)butyl]carbamoyl]pentyl]phosphinyl]methyl]carbamoyl]-3-methylbutyl]carbamate in the form of a white foam.

(ii) 0.75 g of benzyl[(S)-1-[[[methoxy[(RS)-4-methyl-2-[[(S)-3-methyl-1-(methylcarbamoyl)butyl]carbamoyl]pentyl]phosphinyl]methyl]carbamoyl]-3-methylbutyl]carbamate was dissolved in 60 ml of methanol containing 1.4 ml of 1M hydrochloric acid. The solution was hydrogenated over 0.1 g of 10% palladium-on-charcoal for 4 hours. After filtration and evaporation, the residue was re-evaporated three times with 30 ml of toluene each time in order to remove water. The white residue obtained was dissolved in 10 ml of dimethylformamide and the solution was cooled to 0° C. 0.375 g of N-benzyloxycarbonyl-L-proline, 180 mg of N-ethylmorpholine and 0.4 g of hydroxybenzotriazole were added and, after all of the solids had dissolved, 0.345 g of N,N'-dicyclohexylcarbodiimide was added. After stirring at room temperature for 18 hours, the solvent was removed by evaporation. The residue was triturated with 30 ml of ethyl acetate and the mixture was filtered in order to remove dicyclohexylurea. The filtrate was washed twice with 30 ml of saturated sodium hydrogen carbonate solution each time, dried over anhydrous sodium sulfate and evaporated to give a colorless gum which was purified by flash chromatography on silica gel using 15% methanol in ethyl acetate for the elution. There was obtained 0.98 g of benzyl(S)-2-[[(S)-1-[[[methoxy[(RS)-4-methyl-2-[[(S)-3-methyl-1-(methylcarbamoyl)butyl]carbamoyl]pentyl]phosphinyl]methyl]carbamoyl]-3-methylbutyl]carbamoyl]-1-pyrrolidinecarboxylate in the form of a white foam.

(iii) 0.53 g of benzyl(S)-2-[[(S)-1-[[[methoxy[(RS)-4-methyl-2-[[(S)-3-methyl-1-(methylcarbamoyl)butyl]carbamoyl]pentyl]phosphinyl]methyl]carbamoyl]-3-methylbutyl]carbamoyl]-1-pyrrolidinecarboxylate was dissolved in 50 ml of methanol containing 0.8 ml of 1M hydrochloric acid. The solution was hydrogenated over 0.1 g of 10% palladium-on-charcoal for 4 hours. After filtration and evaporation of the filtrate, the residue was re-evaporated three times with 30 ml of toluene each time in order to remove water. The white residue obtained was dissolved in a mixture of 3 ml of dimethylformamide and 10 ml of dichloromethane. The solution was treated with 0.15 g of acetic anhydride and 0.2 g of triethylamine and the mixture was stirred for 2 hours. The solvent was then removed by evaporation. The residue was taken up in 30 ml of ethyl acetate and the mixture was filtered in order to remove triethylamine hydrochloride. The filtrate was then evaporated and the residue was purified by flash chromatography using ethyl acetate/methanol (5:2) for the elution to give 0.43 g of [[[N-(1-acetyl-L-prolyl)-L-leucyl]amino]methyl][(RS)-4-methyl-2-[[(S)-3-methyl-1-methylcarbamoyl)butyl]carbamoyl]pentyl]phosphinic acid methyl ester in the form of a white foam.

(B) THE PROCESS 0.1 g of [[[N-(1-acetyl-L-prolyl)-L-leucyl]amino]methyl][(RS)-4-methyl-2-[[(S)-3-methyl-1-methylcarbamoyl)butyl]carbamoyl]pentyl]phosphinic acid methyl ester was treated according to the procedure described in Example 3(B) to give 95 mg of [[[N-(1-acetyl-L-prolyl)-L-leucyl]amino]methyl][(RS)-4-methyl-2-[[(S)-3-methyl-1-methylcarbamoyl)butyl]carbamoyl]pentyl]phosphinic acid in the form of an off-white foam.

EXAMPLE 10

0.11 g of benzyl(S)-2-[[(S)-1-[[[methoxy[(RS)-4-methyl-2-[[(S)-3-methyl-1-(methylcarbamoyl)butyl]carbamoyl]pentyl]phosphinyl]methyl]carbamoyl]-3-methylbutyl]carbamoyl]-1-pyrrolidinecarboxylate was dissolved in 4 ml of dichloromethane and 0.5 ml of bromotrimethylsilane was added. The mixture was stirred at room temperature for 1.5 hours and the solvent was removed by evaporation. The residue was dissolved in 5 ml of acetone and there were then added 1 ml of water and 0.5 g of sodium hydrogen carbonate followed by 50 mg of benzyl chloroformate. After stirring at room temperature for 2.5 hours, the solvent was removed by evaporation. The residue was dissolved in 15 ml of 1M sodium hydroxide solution and the resulting solution was extracted three times with 15 ml of diethyl ether each time. The aqueous solution was acidified with 10% sulfuric acid, saturated with sodium chloride solution and extracted five times with 20 ml of 5% methanol in dichloromethane each time. The organic extracts were dried over anhydrous sodium sulfate and evaporated to give 0.1 g of [[[N-[1-[(benzyloxy)carbonyl]-L-prolyl]-L-leucyl]amino]methyl][(RS)-4-methyl-2-[[(S)-3-methyl-1-(methylcarbamoyl)butyl]carbamoyl]pentyl]phosphinic acid in the form of a white foam.

EXAMPLE 11

(A) THE PREPARATION OF THE STARTING MATERIAL (i) 1.06 g of L-leucyl-L-alanine ethyl ester hydrochloride and 1.46 g of 2(RS)-[[(RS)-(methoxy)(phthalimidomethyl)-phosphinyl]methyl]-4-methylvaleric acid, prepared as described in Example 1(A)(iii), were dissolved in 12 ml of dimethylformamide. The solution was cooled to 0° C. Thereafter, 1.08 g of hydroxybenzotriazole and 0.46 g of N-ethylmorpholine were added and, after all of the solids had dissolved, 0.88 g of N,N'-dicyclohexylcarbodiimide was added. The mixture was stirred at room temperature for 18 hours. The solvent was then removed by evaporation. The residue was triturated with 50 ml of ethyl acetate and the mixture was filtered in order to remove dicyclohexylurea. The filtrate was washed twice with 50 ml of saturated sodium hydrogen carbonate solution each time, dried over anhydrous sodium sulfate and evaporated to give a yellow gum. This gum was purified by flash chromatography using ethyl acetate for the elution. There were obtained 1.06 g of [(R or S)-2-[[(S)-1-[[(S)-1-(ethoxycarbonyl)ethyl]carbamoyl]-3-methyl-butyl]carbamoyl]-4-methylpentyl](phthalimidomethyl)phosphinic acid methyl ester hydrochloride in the form of a white foam.

(ii) The mixture of the four isomers prepared in paragraph (i) was separated by repeated flash chromatography on silica gel using ethyl acetate for the elution followed by fractional crystallization of enriched fractions from diethyl ether/n-hexane. The four isomers were designated as isomers A, B, C and D in the order of elution from the column.

Isomer A: m.p. 149°–150° C.;
Isomer B: m.p. 164°–165° C.;
Isomer C: m.p. 174°–176° C.;
Isomer D: m.p. 93°–95° C.

(B) THE PROCESS (a) A mixture of 0.1 g of isomers A and B, prepared as described in paragraph (ii) was treated according to the procedure described in Example 3(B) to give 95 mg of [(R or S)-2-[[(S)-1-[[(S)-1-(ethoxycarbonyl)ethyl]carbamoyl]-3-methylbutyl]carbamoyl]-4-methylpentyl](phthalimidomethyl)phosphinic acid in the form of a white foam.

(b) A mixture of 1.0 g of isomers C and D, prepared as described in paragraph (ii), was treated according to the procedure described in Example 3(B) to give 95 mg of [(R or S)-2-[[(S)-1-[(ethoxycarbonyl)ethyl]carbamoyl]-3-methylbutyl]carbamoyl]-4-methylpentyl](phthalimidomethyl)phosphinic acid in the form of a white foam.

EXAMPLE 12

(A) The Preparation of the Starting Material (i) A mixture of 0.65 g of isomers C and D, prepared as described in Example 11(A)(ii), was treated in a manner analogous to that described in Example 2(A)(i) to give 0.47 g of N-[N-[(R or S)-2-[[(aminomethyl)methoxyphosphinyl]methyl]-4-methylvaleryl]-L-leucyl]-L-alanine ethyl ester acetate in the form of a colorless gum.

(ii) 0.45 g of N-[N-[(R or S)-2-[[(aminomethyl)methoxyphosphinyl]methyl]-4-methylvaleryl]-L-leucyl]-L-alanine ethyl ester acetate was treated in a manner analogous to that described in Example 9(A)(i) to give 0.6 g of N-[N-[(R or S)-2-[[[[N-[(benzyloxy)carbonyl]-L-leucyl]amino]methyl]methoxyphosphinyl]methyl]-4-methylvaleryl]-L-leucyl]-L-alanine ethyl ester in the form of a white foam.

(iii) 0.6 g of N-[N-[(R or S)-2-[[[[N-[(benzyloxy)carbonyl]-L-leucyl]amino]methyl]methoxyphosphinyl]methyl]-4-methylvaleryl]-L-leucyl]-L-alanine ethyl ester was treated in a manner analogous to that described in Example 9(A)(ii) to give 0.52 g of N-[N-[(R or S)-2-[[[[N-[1-[(benzyloxy)carbonyl]-L-prolyl]-L-leucyl]amino]methyl]methoxyphosphinyl]methyl]-4-methylvaleryl]-L-leucyl]-L-alanine ethyl ester in the form of a white foam.

(B) The Process 0.11 g of N-[N-[(R or S)-2-[[[[N-[1-[(benzyloxy)carbonyl]-L-prolyl]-L-leucyl]amino]methyl]methoxyphosphinyl]methyl]-4-methylvaleryl]-L-leucyl]-L-alanine was treated in a manner analogous to that described in Example 10 to give 70 mg of N-[N-[(R or S)-2-[[[[N-[1-[(benzyloxy)carbonyl]-L-prolyl]-L-leucyl]amino]methyl]hydroxyphosphinyl]methyl]-4-methylvaleryl]-L-leucyl]-L-alanine in the form of a white foam.

EXAMPLE 13

(A) The Preparation of the Starting Material (i) 0.6 g of [(−)-1-[1-(benzyloxy)formamido]ethyl]phosphinic acid was dissolved in 7 ml of dry tetrahydrofuran containing 0.126 g of ethanol and 0.54 g of N,N'-dicyclohexylcarbodiimide and 0.03 g of dimethylaminopyridine were added. The mixture was stirred at room temperature for 4 hours, filtered and the filtrate was evaporated. The residue was dissolved in 50 ml of ethyl acetate and the solution was washed with 20 ml of 5% potassium hydrogen sulfate solution, then with 20 ml of saturated sodium hydrogen carbonate solution and finally with 20 ml of sodium chloride solution. After drying over magnesium sulfate the solution was evaporated, the residue was dissolved in 20 ml of diethyl ether. The solution was filtered and the filtrate was evaporated to give 0.4 g of an oil; Rf=0.55 (2% methanol in ethyl acetate). This oil was mixed with 0.136 g of 1,1,3,3-tetramethylguanidine and 0.322 g of benzyl isobutylacrylate and the mixture was stirred at room temperature for 18 hours. The mixture was diluted with 25 ml of ethyl acetate and the solution was washed in succession with 10 ml of 10% hydrochloric acid, 10 ml of water and 10 ml of sodium chloride solution. After drying the solvent was removed by evaporation to give an oil which was purified by flash chromatography on silica gel using ethyl acetate for the elution. There was obtained 0.446 g of benzyl (RS)-2-[[[(R or S)-1-[1-(benzyloxy)formamido]ethylethyoxyphosphinyl]methyl]-4-methylvalerate in the form of a colorless oil.

(ii) 0.446 g of benzyl (RS)-2-[[[(R or S)-1-[1-(benzyloxy)formamido]ethyl]ethoxyphosphinyl]methyl]-4-methylvalerate was dissolved in 4 ml of ethanol containing 0.91 ml of 1M sodium hydroxide solution. The mixture was stirred at room temperature for 18 hours and then diluted with 25 ml of water. The solution was washed twice with 25 ml of diethyl ether each time and then acidified by the dropwise addition of concentrated hydrochloric acid. The aqueous solution was extracted three times with 15 ml of ethyl acetate each time and the combined organic extracts were washed with 15 ml of sodium chloride solution, dried over anhydrous sodium sulfate and evaporated to give 0.246 g of a colorless gum. This gum was dissolved in 5 ml of dichloromethane and 0.087 g of L-leucine N-methylamide was added. The solution was cooled to 0° C. and 0.089 g of hydroxybenzotriazole was added. After all of the solid had dissolved, 0.149 g of N,N'-dicyclohexylcarbodiimide was added and the mixture was stirred at room temperature for 18 hours. The solvent was removed by evaporation, the residue was triturated with 25 ml of ethyl acetate and the mixture was filtered in order to remove dicyclohexylurea. The solution was washed with 10 ml of saturated sodium hydrogen carbonate solution, dried over anhydrous sodium sulfate and evaporated to give a gum which was purified by flash chromatography on silica gel using 3% methanol in ethyl acetate for the elution. There was obtained 0.16 g of benzyl[(R or S)-1-[ethoxy-[(RS)-4-methyl-2-[[(S)-3-methyl-1-(methylcarbamoyl)butyl]carbamoyl]pentyl]phosphinyl]ethyl]carbamate in the form of a colorless gum.

(iii) 0.16 g of benzyl[(R or S)-1-[ethoxy-[(RS)-4-methyl-2-[[(S)-3-methyl-1-(methylcarbamoyl)butyl]carbamoyl]pentyl]phosphinyl]ethyl]carbamate was dissolved in 0.28 ml of ethanol containing 1M hydrochloric acid and 0.015 g of 5% palladium-on-charcoal and the mixture was hydrogenated for 2.5 hours. After filtration, the filtrate was evaporated and the residue was re-evaporated twice with 25 ml of dichloromethane each time in order to remove water. The product was dissolved in 5 ml of dry tetrahydrofuran and 0.057 g of triethylamine and 0.046 g of phthalic anhydride were added. The mixture was stirred at room temperature for 2 hours and then 0.076 g of hydroxybenzotriazole and 0.064 g of N,N'-dicyclohexylcarbodiimide were added. After stirring at room temperature for 18 hours, the solvent was removed by evaporation. The residue was triturated with 20 ml of ethyl acetate and the mixture was filtered in order to remove dicyclohexylurea. The filtrate was washed twice with 10 ml of saturated sodium hydrogen carbonate solution each time, dried over anhydrous sodium sulfate and evaporated to give a gum which was purified by flash chromatography on silica gel using 1% methanol in ethyl acetate for the elution. There was obtained 0.078 g of [(RS)-4-methyl-2-[[(S)-3-methyl-1-(methylcarbamoyl)butyl]carbamoyl]pentyl][(R or S)-1-phthalimidoethyl]phosphinic acid ethyl ester in the form of a colorless foam.

(B) The Process 78 mg of [(RS)-4-methyl-2-[[(S)-3-methyl-1-(methylcarbamoyl)butyl]carbamoyl]pentyl][(R or S)-1-phthalimidoethyl]phosphinic acid ethyl ester were treated according to the procedure described in Example 1(B) to give 73 mg of [(RS)-4-methyl-2-[[(S)-3-methyl-1-(methylcarbamoyl)butyl]carbamoyl]pentyl][(R or S)-1-phthalimidoethyl]phosphinic acid in the form of a white foam.

EXAMPLE 14

(A) The Preparation of the Starting Material

In a manner analogous to that described in Example 13(A), from 0.6 g of [(+)-1-[1-(benzyloxy)formamido]ethyl]phosphinic acid there was obtained 0.15 g of [(RS)-4-methyl-2-[[(S)-3-methyl-1-(methylcarbamoyl)butyl]carbamoyl]pentyl][(R or S)-1-phthalimidoethyl]phosphinic acid ethyl ester in the form of a white foam.

(B) The Process 0.1 g of [(RS)-4-methyl-2-[[(S)-3-methyl-1-(methylcarbamoyl)butyl]carbamoyl]pentyl][(R or S)-1-phthalimidoethyl]phosphinic acid ethyl ester was treated according to the procedure described in Example 1(B), to give 95 mg of [(RS)-4-methyl-2-[[(S)-3-methyl-1-(methylcarbamoyl)butyl]carbamoyl]pentyl][(R or S)-1-phthalimidoethyl]phosphinic acid in the form of a white foam.

EXAMPLE 15

(A) The Preparation of the Starting Material (i) Racemic 3-amino-2-azacyclotridecanone was resolved into its optical isomers via the formation of the dibenzoyl tartrate salt followed by successive crystallizations from ethanol. From 13.2 g of the racemic amine and 23.4 g of (−)-dibenzoyltartaric acid there were obtained, after three crystallizations from ethanol, 6.04 g of tartrate salt with $[\alpha]_D^{20} = -115.3°$ (c=1% in methanol).

An analogous procedure using (+)-dibenzoyltartaric acid gave tartrate salt with $[\alpha]_D^{20} = +115.0°$ (c=1% in methanol).

20.0 g of the tartrate salt with $[\alpha]_D^{20} = -115.3°$ were suspended in 400 ml of chloroform and the suspension was shaken with 400 ml of saturated sodium hydrogen carbaonate solution until a clear solution was obtained. After separation of the organic layer, the aqueous solution was extracted with 100 ml of chloroform. The combined organic phases were dried over magnesium sulfate and evaporated to give 7.85 g of (−)-3-amino-2-azacyclotridecanone of melting point 128°–130° C.; $[\alpha]_D^{20} = -63.6°$ (c=1% of methanol).

(ii) In an analogous manner to that described in Example 1(A)(iv), from 0.347 g of 2(RS)-[[(RS)-(methoxy)(phthalimidomethyl)phosphinyl]methyl]-4 -methylvaleric acid and 0.2 g of (−)-3-amino-2-azacyclotridecanone there was obtained 0.21 g of [(RS)-4-methyl-2-[[(R or S)-2-oxoazacyclotridecyl]carbamoyl]pentyl](phthalimidomethyl)phosphinic acid methyl ester in the form of a white solid.

(B) The Process 75 mg of [(RS)-4-methyl-2-[[(R or S)-2-oxoazacyclotridecyl]carbamoyl]pentyl](phthalimidomethyl)phosphinic acid methyl ester were treated according to the procedure described in Example 3(B), paragraph (ii), to give 72 mg of [(RS)-4-methyl-2-[[(R or S)-2-oxoazacyclotridecyl]carbamoyl]pentyl](phthalimidomethyl)phosphinic acid in the form of a white foam.

EXAMPLE 16

(A) The Preparation of the Starting Material

In a manner analogous to that described in Example 3(A), from 0.64 g of (aminomethyl)[(RS)-4-methyl-2-[[(S)-3-methyl-1-(methylcarbamoyl)butyl]carbamoyl]pentyl]phosphinic acid methyl ester acetate and 0.4 g of 3-(benzyloxy)phthalic anhydride, there was obtained 0.347 g of [[3-(benzyloxy)phthalimido]methyl][(RS)-4-methyl-2-[[(S)-3-methyl-1-(methylcarbamoyl)butyl]carbamoyl]pentyl]-phosphinic acid methyl ester in the form of a white foam.

(B) The Process 0.1 g of [[3-(benzyloxy)phthalimido]methyl][(RS)-4-methyl-2-[[(S)-3-methyl-1-(methylcarbamoyl)butyl]carbamoyl]pentyl]phosphinic acid methyl ester was treated according to the procedure described in Example 3(B) to give 95 mg of [[3-(benzyloxy)phthalimido]methyl][(RS)-4-methyl-2-[[(S)-3-methyl-1-(methylcarbamoyl)butyl]carbamoyl]pentyl]phosphinic acid in the form of a white foam.

EXAMPLE 17

0.2 g of [[3-(benzyloxy)phthalimido]methyl][(RS)-4-methyl-2-[[(S)-3-methyl-1-(methylcarbamoyl)butyl]carbamoyl]pentyl]phosphinic acid was dissolved in 50 ml of methanol containing 0.1 g of 10% palladium-on-charcoal. The mixture was hydrogenated for 4 hours and then filtered. The filtrate was evaporated to give 0.16 g of [[(3-hydroxyphthalimido)methyl][(RS)-4-methyl-2-[[(S)-3-methyl-1-(methylcarbamoyl)butyl]carbamoyl]pentyl]phosphinic acid in the form of an off-white foam.

EXAMPLE 18

(A) The Preparation of the Starting Material

In a manner analogous to that described in Example 3(A), from 0.23 g of (aminomethyl)[(RS)-4-methyl-2-[[(S)-3-methyl-1-(methylcarbamoyl)butyl]carbamoyl]pentyl]phosphinic acid methyl ester acetate and 0.105 g of 3-nitrophthalic anhydride, there was obtained 0.105 g of [4-methyl-2-(methylcarbamoyl)butyl]carbamoyl]pentyl][(3-nitrophthalimido)methyl]phosphinic acid methyl ester in the form of a pale yellow foam.

(B) The Process 0.1 g of [4-methyl-2-[[3-methyl-1-(methylcarbamoyl)butyl]carbamoyl]pentyl][(3-nitrophthalimido)methyl]phosphinic acid methyl ester was treated according to the procedure described in Example 3(B) to give 95 mg of [4-methyl-2-[[3-methyl-1-(methylcarbamoyl)butyl]carbamoyl]pentyl][(3-nitrophthalimido)methyl]phosphinic acid in the form of a pale yellow foam.

EXAMPLE 19

75 mg of [4-methyl-2-[[3-methyl-1-(methylcarbamoyl)butyl]carbamoyl]pentyl][(3-nitrophthalimido)methyl]phosphinic acid were dissolved in 2.5 ml of methanol containing 0.01 g of 10% palladium-on-charcoal. The mixture was hydrogenated for 3 hours and then filtered. The filtrate was evaporated to give 70 mg of [(3-aminophthalimido)methyl][(RS)-4-methyl-2-[[(S)-3-methyl-1-(methylcarbamoyl)butyl]carbamoyl]pentyl]phosphinic acid in the form of a yellow foam.

EXAMPLE 20

(A) The Preparation of the Starting Material (i) In a manner analogous to that described in Example 1(A)(i)–(iv), from 10.95 g of crystalline phosphinic acid acid, 10.99 g of benzyl isobutylacrylate and 30.31 g of triethyl orthoformate there were obtained 3.2 g of [(RS)-4-methyl-2-[[(S)-3-methyl-1-(methylcarbamoyl)butyl]carbamoyl]-4-methylpentyl](phthalimidomethyl)phosphinic acid ethyl ester in the form of a white foam.

(ii) 3.2 g of [(RS)-4-methyl-2-[[(S)-3-methyl-1-(methylcarbamoyl)butyl]carbamoyl]-4-methylpentyl](phthalimidomethyl)phosphinic acid ethyl ester were treated in a manner analogous to that described in Example 2(A)(i), with the exception that a 0.33M solution of hydrazine hydrate in ethanol was used, to give 2.06 g of (aminomethyl)[(RS)-4-methyl-2-[[(S)-3-methyl-1-(methylcarbamoyl)butyl]carbamoyl]pentyl]phosphinic acid ethyl ester acetate in the form of a white foam.

(iii) In a manner analogous to that described in Example 3(A), from 0.52 g of (aminomethyl)[(RS)-4-methyl-2-[[(S)-3-methyl-1-(methylcarbamoyl)butyl]carbamoyl]pentyl]phosphinic acid ethyl ester acetate and 0.34 g of diphenylmaleic anhydride, there was obtained 0.581 g of [(2,3-diphenylmaleimido)methyl][(RS)-4-methyl-2-[[(S)-3-methyl-1-(methylcarbamoyl)butyl]carbamoyl]pentyl]phosphinic acid ethyl ester in the form of a yellow-green foam.

The Process 0.1 g of [(2,3-diphenylmaleimido)methyl][(RS)-4-methyl-2-[[(S)-3-(methylcarbamoyl)butyl]carbamoyl]pentyl]phosphinic acid ethyl ester was treated according to the procedure described in Example 4(B) to give 95 mg of [(2,3-diphenylmaleimido)methyl][(RS)-4-methyl-2-[[(S)-3-methyl-1-(methylcarbamoyl)butyl]carbamoyl]pentyl]phosphinic acid in the form of a yellow-green foam.

EXAMPLE 21

(A) The Preparation of the Starting Material

In a manner analogous to that described in Example 3(A), from 0.5 g of (aminomethyl)[(RS)-4-methyl-2-[[(S)-3-methyl-1-(methylcarbamoyl)butyl]carbamoyl]pentyl]phosphinic acid ethyl ester acetate and 0.27 g of 3,6-dimethoxyphthalic anhydride, there was obtained 0.325 g of [(3,6-dimethoxyphthalimido)methyl][(RS)-4-methyl-2-[[(S)-3-methyl-1-(methylcarbamoyl)butyl]carbamoyl]pentyl]phosphinic acid ethyl ester in the form of a pale yellow foam.

(B) The Process 0.1 g of [(3,6-dimethoxyphthalimido)methyl][(RS)-4-methyl-2-[[(S)-3-methyl-1-(methylcarbamoyl)butyl]carbamoyl]pentyl]phosphinic acid ethyl ester was treated according to the procedure described in Example 3(B) to give 95 mg of [(3,6-dimethoxyphthalimido)methyl][(RS)-4-methyl-2-[[(S)-3-methyl-1-(methylcarbamoyl)butyl]carbamoyl]pentyl]phosphinic acid in the form of a yellow foam.

EXAMPLE 22

(A) The Preparation of the Starting Material

In a manner analogous to that described in Example 3(A), from 0.528 g of (aminomethyl)[(RS)-4-methyl-2-[[(S)-3-methyl-1-(methylcarbamoyl)butyl]carbamoyl]pentyl]phosphinic acid ethyl ester acetate and 0.273 g of 2,3-naphthalic anhydride, there was obtained 0.387 g of [(RS)-4-methyl-2-[[(S)-3-methyl-1-(methylcarbamoyl)butyl]carbamoyl]pentyl](2,3-naphthalenedicarboximidomethyl)phosphinic acid ethyl ester in the form a white foam.

(B) The Process 0.1 g of [(RS)-4-methyl-2-[[(S)-3-methyl-1-(methylcarbamoyl)butyl]carbamoyl]pentyl](2,3-naphthalenedicarboximidomethyl)phosphinic acid ethyl ester was treated according to the procedure described in Example 3(B) to give 95 mg of [(RS)-4-methyl-2-[[(S)-3-methyl-1-(methylcarbamoyl)butyl]carbamoyl]pentyl](2,3-naphthalenedicarboximidomethyl)phosphinic acid in the form of a white foam.

EXAMPLE 23

(A) The Preparation of the Starting Material (i) In a manner analogous to that described in Example 1(A)(iv), from 1.9 g of 2(RS)-[[(RS)-(ethoxy)(phthalimidomethyl)phosphinyl]methyl]-4-methylvaleric acid and 1.0 g of (−)-3-amino-2-azacyclotridecanone, there were obtained 2.1 g of 2(RS)-[[(RS)-(ethoxy)(phthalimidomethyl)phosphinyl]methyl]-4-methyl-N(R or S)-(2-oxoazacyclotridecan-3-yl)valeramide in the form of a white solid.

(ii) The mixture of the four isomers prepared as described in the preceding paragraph was separated by repeated flash chromatography on silica gel using 30% acetone in dichloromethane for the elution. The four isomers were designated as isomers A, B, C and D in the order of elution from the column. From 3.5 g of the mixture, there was obtained 1 g of a mixture of isomers B and C.

(iii) 0.5 g of a mixture of isomers B and C was treated in a manner analogous to that described in Example 20(A)(ii) to give (aminomethyl)[(R or S)-4-methyl-2-[(R or S)-2-oxo-3-azacyclotridecyl]carbamoyl]pentyl]phosphinic acid ethyl ester acetate in the form of a white gum which was then treated with 0.2 g of 1,8-naphthalic anhydride in a manner analogous to that described in Example 3(A) to give 0.355 g of [(R or S)-4-methyl-2-[[(R or S)-2-oxo-3-azacyclotridecyl]carbamoyl]pentyl](1,8-naphthalenedicarboximidomethyl)phosphinic acid ethyl ester in the form of a white solid.

(B) The Process 0.16 g of [(R or S)-4-methyl-2-[[(R or S)-2-oxo-3-azacyclotridecyl]carbamoyl]pentyl](1,8-naphthalenedicarboximidomethyl)phosphinic acid ethyl ester was dissolved in of 2 ml of acetic acid containing 48% hydrogen bromide and the solution was stirred at room temperature for 18 hours. After evaporation, the solid residue was triturated with 20 ml of diethyl ether. The solid was removed by filtration and dried in vacuo at 60° C. to give 0.145 g of [(R or S)-4-methyl-2-[[(R or S)-2-oxo-3-azacyclotridecyl]carbamoyl]pentyl](1,8-naphthalenedicarboximidomethyl)phosphinic acid in the form of a white powder of melting point 268°–269° C.

EXAMPLE 24

(A) The Preparation of the Starting Material 0.155 g (1 mmol) of isobutylmaleic anhydride and 0.42 g (1 mmol) of (aminomethyl)[(RS)-4-methyl-2-[[(S)-3-methyl-1-(methylcarbamoyl)butyl]carbamoyl]pentyl]phosphinic acid methyl ester acetate were dissolved in 5 ml of dry tetrahydrofuran and the solution was stirred at room temperature for 2 hours in the presence of 0.202 g (2 mmol) of triethylamine. Subsequently, 0.27 g (2 mmol) of hydroxybenzotriazole and 0.206 g (1 mmol) of N,N'-dicyclohexylcarbodiimide were added. The mixture was stirred at room temperature for 18 hours. Dicyclohexylurea was removed by filtration and the filtrate was evaporated. The residue was taken up in 50 ml of ethyl acetate and the solution was washed in sequence with 5% citric acid solution and saturated sodium hydrogen carbonate solution and then dried over anhydrous sodium sulfate. After removal of the solvent by evaporation, there was obtained 0.35 g of a solid which was chromatographed on silica gel using 1% methanol in chloroform for the elution. There were obtained 165 mg of [(2-isobutylmaleimido)methyl][(RS)-4-methyl-2-[[(S)-3-methyl-1-(methylcarbamoyl)butyl]carbamoyl]pentyl]phosphinic acid methyl ester in the form of a foam.

(B) The Process 0.145 g (0.29 mmol) of [(2-isobutylmaleimido)methyl][(RS)-4-methyl-2-[[(S)-3-methyl-1-(methylcarbamoyl)butyl]carbamoyl]pentyl]phosphinic acid methyl ester was dissolved in 3 ml of trifluoroacetic acid and the solution was stirred at room temperature for 5 hours. After evaporation, the crude product was chromatographed on silica gel using chloroform/methanol/acetic acid/water (120:15:3:2) for the elution. There were obtained 70 mg of [(2-isobutylmaleimido)methyl][(RS)-4-methyl-2-[[(S)-3-methyl-1-(methylcarbamoyl)butyl]carbamoyl]pentyl]phosphinic acid in the form of a foam.

EXAMPLE 25

(A) The Preparation of the Starting Material

In a manner analogous to that described in Example 24(A), from 0.161 g (1.41 mmol) of glutaric anhydride and 0.41 g (0.94 mmol) of (aminomethyl)[(RS)-4-methyl-2-[[(S)-3-methyl-1-(methylcarbamoyl)butyl]carbamoyl]pentyl]phosphinic acid ethyl ester acetate, there was obtained 0.124 g of (glutarimidomethyl)[(RS)-4-methyl-2-[[(S)-3-methyl-1-(methylcarbamoyl)butyl]carbamoyl]pentyl]phosphinic acid ethyl ester.

(B) The Process 0.11 g (0.23 mmol) of (glutarimidomethyl)[(RS)-4-methyl-2-[[(S)-3-methyl-1-(methylcarbamoyl)butyl]carbamoyl]pentyl]phosphinic acid ethyl ester was dissolved in 4 ml of dicloromethane and the solution was stirred overnight in the presence of 2 ml of bromotrimethylsilane. The solvent was removed by evaporation and the residue was dissolved in 5 ml of acetone/water (9:1). The solvent was removed by evaporation and this treatment was repeated once more to give 0.1 g of (glutarimidomethyl)[(RS)-4-methyl-2-[[(S)-3-methyl-1-(methylcarbamoyl)butyl]carbamoyl]pentyl]phosphinic acid in the form of a foam.

EXAMPLE 26

(A) The Preparation of the Starting Material

In a manner analogous to that described in Example 24(A), from 0.17 g (1.09 mmol) of 2(S)-isobutylsuccinic anhydride and 0.32 g (0.73 mmol) of (aminomethyl)[(RS)-4-methyl-2-[[(S)-3-methyl-1-(methylcarbamoyl)butyl]carbamoyl]pentyl]phosphinic acid ethyl ester acetate, there was obtained 0.16 g of [[(S)-2-isobutylsuccinimido]methyl][(RS)-4-methyl-2-[[(S)-3-methyl-1-(methylcarbamoyl)butyl]carbamoyl]pentyl]-phosphinic acid ethyl ester.

(B) The Process

The product obtained according to the preceding paragraph in 2 ml of dichloromethane was treated overnight with 2 ml of bromotrimethylsilane. The solvent was removed by evaporation and the residue was treated with 5 ml of acetone/water (9:1). The solvent was removed by evaporation and the crude product was purified by chromatography on silica gel using chloroform/methanol/acetic acid/water (90:21:3:2) for the elution to give 0.09 g of [[(S)-2-isobutylsuccinimido]methyl][(S)-4-methyl-2-[[(S)-3-methyl-1-(methylcarbamoyl)butyl]carbamoyl]pentyl]phosphinic acid.

The 2(S)-isobutylsuccinnic anhydride used in part (A) of this Example was prepared as follows:

(i) 2.5 g (8.1 mmol) of 1-(4-nitrobenzyl) hydrogen 2(S)-isobutylsuccinnate were dissolved in 10 ml of tetrahydrofuran and the solution was stirred at room temperature for 3 hours in the presence of 4 ml of 4M sodium hydroxide solution. The solvent was removed by evaporation. The residue was dissolved in 20 ml of water and the solution was extracted three times with 25 ml of diethyl ether each time. The aqueous solution was acidified with 2M hydrochloric acid and the product was extracted with diethyl ether. The diethyl ether extracts were washed with saturated sodium chloride solution and dried over anhydrous sodium sulfate. The solvent was removed by evaporation to yield 1.3 g of 2(S)-isobutylsuccinnic acid in the form of a gum.

(ii) 0.19 g (1.1 mmol) of 2(S)-isobutylsuccinnic acid was dissolved in 5 ml of dichloromethane and the solution was cooled to 0° C. thereafter, 0.225 g (1.1 mmol) of N,N'-dicyclohexylcarbodiimide was added and the mixture was stirred at room temperature overnight. Dicyclohexylurea was removed by filtration and the filtrate was evaporated to give 0.17 g of 2(S)-isobutylsuccinnic anhydride in the form of a gum; IR 1800 $cm^{-1}$.

EXAMPLE 27

In a manner analogous to that described in Example 26, there was prepared [[(R)-2-isobutylsuccinimido]methyl][(RS)-4-methyl-2-[[(S)-3-methyl-1-(methylcarbamoyl)butyl]carbamoyl]pentyl]phosphinic acid.

EXAMPLE 28

(A) The Preparation of the Starting Material (i) 3 g (6.4 mmol) of benzyl 2(RS)-[[(RS)-(ethoxy)(phthalimidomethyl)phosphinyl]methyl]-4-methylvalerate were dissolved in 39 ml (12.8 mmol) of a 0.33M solution of hydrazine hydrate in ethanol. The solution was stirred at room temperature overnight. The solvent was removed by evaporation and traces of hydrazine were removed by treatment with toluene followed by evaporation. The residue was taken up in 50 ml of dichloromethane and stirred at room temperature for 45 minutes in the presence of 5 ml of glacial acetic acid. The solid was removed by filtration and the filtrate was evaporated to give 2.56 g of benzyl 2(RS)-[[(RS)-(aminomethyl)(ethoxy)phosphinyl]methyl]-4-methylvalerate in the form of a gum.

(ii) 1.3 g (6.34 mmol) of phthalylglycine were dissolved in 10 ml of tetrahydrofuran. The solution was cooled in an ice-salt bath and then treated with 0.86 g (6.4 mmol) of hydroxybenzotriazole and 1.3 g (6.4 mmol) of N,N'-dicyclohexylcarbodiimide. The mixture was stirred at room temperature for 5 hours and dicyclohexylurea was then removed by filtration. The filtrate was evaporated. The resulting gum was dissolved in 10 ml of tetrahydrofuran and the solution was treated at 0° C. with 2.5 g (6.2 mmol) of benzyl 2(RS)-[[(RS)-(aminomethyl)(ethoxy)phosphinyl]methyl]-4-methylvalerate and 0.75 g (6.5 mmol) of N-ethylmorpholine. The solution was stirred at room temperature overnight and the solvent was removed by filtration. The residue was taken up in 100 ml ethyl acetate, washed in sequence with 5% citric acid solution, 5% sodium hydrogen carbonate solution and water, dried over anhydrous sodium sulfate and evaporated to give a gum. Chromatography of this gum on silica gel using chloroform/methanol (98:2) for the elution gave 0.95 g of benzyl 2(RS)-[[(RS)-(ethoxy)[(2-phthalimidoacetamido)methyl]phosphinyl]methyl]-4-methylvalerate.

(iii) 0.95 g (1.8 mmol) of benzyl 2(RS)-[[(RS)-(ethoxy)[(2-phthalimidoacetamido)methyl]phosphinyl]methyl]-4-methylvalerate was treated with 11 ml (3.6 mmol) of a 0.33M solution of hydrazine hydrate in ethanol. After stirring at room temperature overnight, the mixture was worked-up as described in paragraph (i) of this Example. Purification by chromatography on silica gel using chloroform/methanol/acetic acid/water (120:15:3:2) for the elution gave 0.43 g of benzyl 2(RS)-[[[(RS)-(2-aminoacetamido)methyl](ethoxy)phosphinyl]methyl]-4-methylvalerate acetate in the form of a gum.

(iv) 0.4 g (0.87 mmol) of benzyl 2(RS)-[[[(RS)-(2-aminoacetamido)methyl](ethoxy)phosphinyl]methyl]-4-methylvalerate acetate was dissolved in 170 ml of dry toluene. The solution was heated at 110° C. in the presence of 0.125 g (1.24 mmol) of triethylamine and 4 ml (7.72 mmol) of a 1.93M solution of phosgene in toluene. After 15 minutes, the solvent was removed by evaporation. The residue was dissolved in 10 ml of dry toluene and the solution was evaporated. The residue was then dissolved in 5 ml of dry dichloromethane and the solution was stirred at room temperature for 2 hours in the presence of 0.125 g (1.24 mmol) of triethylamine. Thereafter, 25 ml of dichloromethane were added and the solution was washed with water and sodium chloride solution, dried over anhydrous sodium sulfate and evaporated to give a gum. Chromatography of this gum on silica gel using chloroform/methanol (19:1) for the elution gave 0.3 g of benzyl 2(RS)-[[(RS)-(ethoxy)[(2,5-dioxo-1-imidazolidinyl)methyl]phosphinyl]-methyl]-4-methylvalerate in the form of a gum.

(v) 0.27 g (0.64 mmol) of benzyl 2(RS)-[[(RS)-(ethoxy)[(2,5-dioxo-1-imidazolidinyl)methyl]phosphinyl]methyl]-4-methylvalerate was dissolved in 10 ml of ethanol and the solution was hydrogenated in the presence of 0.2 g of 10% palladium/carbon at room temperature and under atmospheric pressure. After 1 hour, the catalyst was removed by filtration and the solvent was evaporated to give 0.22 g of 2(RS)-[[(RS)-(ethoxy)[(2,5-dioxo-1-imidazolidinyl)methyl]phosphinyl]methyl]-4-methylvaleric acid in the form of a foam;

(vi) 0.22 g (0.64 mmol) of 2(RS)-[[(RS)-(ethoxy)[(2,5-dioxo-1-imidazolidinyl)methyl]phosphinyl]methyl]-4-methylvaleric acid and 0.116 g (0.81 mmol) of L-leucine methylamide were taken up in 5 ml of dichloromethane and 2.5 ml of tetrahydrofuran. The solution was treated at −8° C. with 0.3 g (1.2 mmol) of N-ethoxycarbonyl-2-ethoxy-1,2-dihydroxyquinoline. The mixture was stirred at room temperature for 24 hours and was then left to stand at 0° C. for 48 hours. The solvent was removed by evaporation. The residue was taken up in 50 ml of chloroform. The solution was washed in sequence with 5% citric acid solution, 5% sodium hydrogen carbonate solution and sodium chloride solution, dried over anhydrous sodium sulfate and evaporated to give a gum. This gum was chromatographed on silica gel using chloroform/methanol (19:1) for the elution to give 0.08 g of [(2,5-dioxo-1-imidazolidinyl)methyl][(RS)-4-methyl-2-[[(S)-3-methyl-1-(methylcarbamoyl)butyl]carbamoyl]pentyl]phosphinic acid ethyl ester as a gum.

(B) The Process 60 mg (0.13 mmol) of [(2,5-dioxo-1-imidazolidinyl)methyl][(RS)-4-methyl-2-[[(S)-3-methyl-1-(methylcarbamoyl)butyl]carbamoyl]pentyl]phosphinic acid ethyl ester were dissolved in 1 ml of dichloromethane and the solution was stirred at room temperature for 3 hours in the presence of 1 ml of bromotrimethylsilane and 0.1 ml of trifluoroacetic acid. The solvent was removed by evaporation. The residue was treated three times with acetone/water (9:1) and the solvent was removed by evaporation each time. Finally, the product was triturated with diethyl ether to yield 55 mg of [(2,5-dioxo-1-imidazolidinyl)methyl][(RS)-4-methyl-2-[[(S)-3-methyl-1-(methylcarbamoyl)butyl]carbamoyl]pentyl]phosphinic acid in the form of a foam.

EXAMPLE 29

In an analogous manner to that described in Example 4(B), from [[1,4-dihydro-2,4-dioxo-3-(2H)-quinazolinyl]methyl][(RS)-4-methyl-2-[[(S)-3-methyl-1-(methylcarbamoyl)butyl]carbamoyl]pentyl]phosphinic acid ethyl ester, there was obtained [[1,4-dihydro-2,4-dioxo-3-(2H)quinazolinyl]methyl][(RS)-4-methyl-2-[[(S)-3-methyl-1-(methylcarbamoyl)butyl]carbamoyl]pentyl]phosphinic acid in the form of a pale yellow foam;

from [[1,4-dihydro-2,4-dioxo-3-(2H)-quinazolinyl]methyl][(R or S)-4-methyl-2-[[(R or S)-2-oxo-3-azacyclotridecyl]carbamoyl]pentyl]phosphinic acid ethyl ester, there was obtained [[1,4-dihydro-2,4-dioxo-3(2H)-quinazolinyl]methyl][(R or S)-4-methyl-2-[[(R or S)-2-oxo-3-azacyclotridecyl]carbamoyl]pentyl]phosphinic acid in the form of an off-white foam;

from [[2,4-dioxo-2H-1,3-benzoxazin-3(4H)-yl]methyl][(RS)-4-methyl-2-[[(S)-3-methyl-1-(methylcarbamoyl)butyl]carbamoyl]pentyl]phosphinic acid ethyl ester, there was obtained [[2,4-dioxo-2H-1,3-benzoxazin-3(4H)-yl]methyl][(RS)-4-methyl-2-[[(S)-3-methyl-1-(methylcarbamoyl)butyl]carbamoyl]pentyl]phosphinic acid in the form of an off-white foam;

from [(RS)-4-methyl-2-[[(S)-3-methyl-1-(methylcarbamoyl)butyl]carbamoyl]pentyl][[3,5-dioxo-4H-thieno[3,4-c]pyrrol-5(6H)-yl]methyl]phosphinic acid ethyl ester, there was obtained [(RS)-4-methyl-2-[[(S)-3-methyl-1-(methylcarbamoyl)butyl]carbamoyl]pentyl][[3,5-dioxo-4H-thieno[3,4-c]pyrrol-5(6H)-yl]methyl]phosphinic acid in the form of a cream foam;

from [[1,4-dihydro-1-methyl-2,4-dioxo-3(2H)-quinazolinyl]methyl][(RS)-4-methyl-2-[[(S)-3-methyl-1-(methylcarbamoyl)butyl]carbamoyl]pentyl]phosphinic acid ethyl ester, there was obtained [[1,4-dihydro-1-methyl-2,4-dioxo-3(2H)-quinazolinyl]methyl][(RS)-4-methyl-2-[[(S)-3-methyl-1-(methylcarbamoyl)butyl]carbamoyl]pentyl]phosphinic acid in the form of a white foam;

from [(4-amino-1,8-naphthalenedicarboximido)methyl][(RS)-4-methyl-2-[[(S)-3-methyl-1-(methylcarbamoyl)butyl]carbamoyl]pentyl]phosphinic acid methyl ester, there was obtained [(4-amino-1,8-naphthalenedicarboximido)methyl][(RS)-4-methyl-2-[[(S)-3-methyl-1-(methylcarbamoyl)butyl]carbamoyl]pentyl]phosphinic acid in the form of an orange foam;

from [(4-amino-3-bromo-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(4-amino-3-bromo-1,8-naphthalenedicarboximido)methyl][(RS)-4-methyl-2-[[(S)-3-methyl-1-(methylcarbamoyl)butyl]carbamoyl]pentyl]phosphinic acid in the form of a yellow foam;

from [(4-amino-3-chloro-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(4-amino-3-chloro-1,8-naphthalenedicarboximido)methyl][(RS)-4-methyl-2-[[(S)-3-methyl-1-(methylcarbamoyl)butyl]carbamoyl]pentyl]phosphinic acid in the form of a yellow powder;

from [(4-amino-3-jodo-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(4-amino-3-jodo-1,8-naphthalenedicarboximido)methyl][(RS)-4-methyl-2-[[(S)-3-methyl-1-(methylcarbamoyl)butyl]carbamoyl]pentyl]phosphinic acid in the form of an orange-yellow powder;

from [(3-amino-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(3-amino-1,8-naphthalenedicarboximido)methyl][(RS)-4-methyl-2-[[(S)-3-methyl-1-(methylcarbamoyl)butyl]carbamoyl]pentyl]phosphinic acid in the form of an orange foam;

from [(RS)-4-methyl-2-[[(R or S)-2-oxo-3-azacyclotridecyl]carbamoyl]pentyl][(1,8-naphthalenedicarboximido)methyl]phosphinic acid ethyl ester, there was obtained [(RS)-4-methyl-2-[[(R or S)-2-oxo-3-azacyclotridecyl]carbamoyl]pentyl][(1,8-naphthalenedicarboximido)methyl]phosphinic acid in the form of a white powder;

from [(RS)-4-methyl-2-[[(S)-3-methyl-1-(methylcarbamoyl)butyl]carbamoyl]pentyl][[1,3,6,7-tetrahydro-1,3-dioxo-2H-indeno[6,7,1-def]isoquinolin-2-yl]methyl]phosphinic acid ethyl ester, there was obtained [(RS)-4-methyl-2-[[(S)-3-methyl-1-(methylcarbamoyl)butyl]carbamoyl]-pentyl][[1,3,6,7-tetrahydro-1,3-dioxo-2H-indeno[6,7,1-def]isoquinolin-2-yl]methy;]phosphinic acid in the form of a pale cream foam;

from [(3,6-dinitro-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(3,6-dinitro-1,8-naphthalenedicarboximido)methyl][(RS)-4-methyl-2-[[(S)-3-methyl-1-(methylcarbamoyl)butyl]carbamoyl]pentyl]phosphinic acid in the form of a white foam;

from [(4-amino-3-bromo-1,8-naphthalenedicarboximido)methyl][(R or S)-4-methyl-2-[[(R or S)-2-oxo-3-azacyclotridecyl]carbamoyl]pentyl]phosphinic acid ethyl ester, there was obtained [(4-amino-3-bromo-1,8-naphthalenedicarboximido)methyl][(R or S)-4-methyl-2-[[(R or S)-2-oxo-3-azacyclotridecyl]carbamoyl]pentyl]phosphinic acid in the form of a yellow powder of melting point 277°–280° C. (decomposition);

from [[6-amino-5-bromo-1H-benz[d,e]isoquinolin-2(3H)-yl]methyl][(R or S)-4-methyl-2-[[(S)-3-methyl-1-(methylcarbamoyl)butyl]carbamoyl]pentyl]phosphinic acid ethyl ester, there was obtained [[6-amino-5-bromo-1H-benz[d,e]isoquinolin-2(3H)-yl]methyl][(R or S)-4-methyl-2-[[(S)-3-methyl-1-(methylcarbamoyl)butyl]carbamoyl]pentyl]phosphinic acid in the form of a yellow powder;

from [(3-bromo-1,8-naphthalenedicarboximido)methyl][(R or S)-4-methyl-2-[[(S)-3-methyl-1-(methylcarbamoyl)butyl]carbamoyl]pentyl]phosphinic acid ethyl ester, there was obtained [(3-bromo-1,8-naphthalenedicarboximido)methyl][(R or S)-4-methyl-2-[[(S)-3-methyl-1-(methylcarbamoyl)butyl]carbamoyl]pentyl]phosphinic acid in the form of a white powder;

from [(3,6-diamino-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(3,6-diamino-1,8-naphthalenedicarboximido)methyl][(RS)-4-methyl-2-[[(S)-3-methyl-1-(methylcarbamoyl)butyl]carbamoyl]pentyl]phosphinic acid trifluoracetate in the form of an orange foam;

from [(RS)-4-methyl-2-[[(S)-3-methyl-1-(methylcarbamoyl)butyl]carbamoyl]pentyl][(4-nitro-1,8-naphthalenedicarboximido)methyl]phosphinic acid ethyl ester, there was obtained [(RS)-4-methyl-2-[[(S)-3-methyl-1-(methylcarbamoyl)butyl]carbamoyl]pentyl][(4-nitro-1,8-naphthalenedicarboximido)methyl]phosphinic acid in the form of an off-white foam;

from [(2-amino-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(2-amino-1,8-naphthalenedicarboximido)methyl][(RS)-4-methyl-2-[[(S)-3-methyl-1-(methylcarbamoyl)butyl]carbamoyl]pentyl]phosphinic acid in the form of an orange foam;

from [(4-benzyloxy-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(4-benzyloxy-1,8-naphthalenedicarboximido)methyl][(RS)-4-methyl-2-[[(S)-3-methyl-1-(methylcarbamoyl)butyl]carbamoyl]pentyl]phosphinic acid in the form of an off-white foam;

from [(4-hydroxy-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(4-hydroxy-1,8-naphthalenedicarboximido)methyl][(RS)-4-methyl-2-[[(S)-3-methyl-1-(methylcarbamoyl)butyl]carbamoyl]pentyl]phosphinic acid in the form of a pale yellow foam;

from [(3,6-diacetamido-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(3,6-diacetamido-1,8-naphthalenedicarboximido)methyl][(RS)-4-methyl-2-[[(S)-3-methyl-1-(methylcarbamoyl)butyl]carbamoyl]pentyl]phosphinic acid in the form of a pale yellow foam;

from [(3,6-dihydroxy-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(3,6-dihydroxy-1,8-naphthalenedicarboximido)methyl][(RS)-4-methyl-2-[[(S)-3-methyl-1-(methylcarbamoyl)butyl]carbamoyl]pentyl]phosphinic acid in the form of a yellow foam;

from [(3-hydroxy-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(3-hydroxy-1,8-naphthalenedicarboximido)methyl][(RS)-4-methyl-2-[[(S)-3-methyl-1-(methylcarbamoyl)butyl]carbamoyl]pentyl]phosphinic acid in the form of a yellow foam;

from [(4-hydroxy-1,8-naphthalenedicarboximido)methyl][(RS)-4-methyl-2-[[(R or S)-2-oxo-3-azacyclotridecyl]carbamoyl]pentyl]phosphinic acid ethyl ester, there was obtained [(4-hydroxy-1,8-naphthalenedicarboximido)methyl][(RS)-4-methyl-2-[[(R or S)-2-oxo-3-azacyclotridecyl]carbamoyl]pentyl]phosphinic acid in the form of a yellow solid of melting point 230°–231° C.;

from [(4-hydroxy-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(4-hydroxy-1,8-naphthalenedicarboximido)methyl][(RS)-4-methyl-2-[[(S)-3-methyl-1-(methylcarbamoyl)butyl]carbamoyl]pentyl]phosphinic acid in the form of a yellow powder of melting point 185°–193° C.;

from [(3-hydroxy-4-nitro-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(3-hydroxy-4-nitro-1,8-naphthalenedicarboximido)methyl][(RS)-4-methyl-2-[[(S)-3-methyl-1-(methylcarbamoyl)butyl]carbamoyl]pentyl]phosphinic acid in the form of a yellow foam;

from [(3-bromo-4-hydroxy-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(3-bromo-4-hydroxy-1,8-naphthalenedicarboximido)methyl][(RS)-4-methyl-2-[[(S)-3-methyl-1-(methylcarbamoyl)butyl]carbamoyl]pentyl]phosphinic acid in the form of yellow solid;

from [(3-hydroxy-1,8-naphthalenedicarboximido)methyl][(RS)-4-methyl-2-[[(R or S)-2-oxo-3-azacyclotridecyl]carbamoyl]pentyl]phosphinic acid ethyl ester, there was obtained [(3-hydroxy-1,8-naphthalenedicarboximido)methyl][(RS)-4-methyl-2-[[(R or S)-2-oxo-3-azacyclotridecyl]carbamoyl]pentyl]phosphinic acid in the form of a hygroscopic powder of melting point >250° C.;

from [(3-bromo-4-hydroxy-1,8-naphthalenedicarboximido)methyl][(RS)-4-methyl-2-[[(R or S)-2-oxo-3-azacyclotridecyl]carbamoyl]pentyl]phosphinic acid ethyl ester, there was obtained [(3-bromo-4-hydroxy-1,8-naphthalenedicarboximido)methyl][(RS)-4-methyl-2-[[(R or S)-2-oxo-3-azacyclotridecyl]carbamoyl]pentyl]phosphinic acid in the form of a pale yellow solid of melting point 251°-252° C.; and from [(3,6-dihydroxy-1,8-naphthalenedicarboximido)methyl][(RS)-4-methyl-2-[[(R or S)-2-oxo-3-azacyclotridecyl]carbamoyl]pentyl]phosphinic acid ethyl ester, there was obtained [(3,6-dihydroxy-1,8-naphthalenedicarboximido)methyl][(RS)-4-methyl-2-[[(R or S)-2oxo-3-azacyclotridecyl]carbamoyl]pentyl]phosphinic acid in the form of a pale yellow powder of melting point 280°-282° C.

EXAMPLE 30

In an analogous manner to that described in Example 10, from [[N-[1-[(benzyloxy)carbonyl]-L-prolyl]-L-leucyl]amino]methyl][(RS)-4-methyl-2-[[(R or S)-2-oxo-3-azacyclotridecyl]carbamoyl]pentyl]phosphinic acid ethyl ester there was obtained [[[N-[1-[(benzyloxy)carbonyl]-L-prolyl]-L-leucyl]amino]methyl][(RS)-4-methyl-2-[[(R or S)-2-oxo-3-azacyclotridecyl]carbamoyl]pentyl]phosphinic acid in the form of a white foam;

from [(R)-1-[[N-[1-[(benzyloxy)carbonyl]-L-prolyl]-D-leucyl]amino]ethyl][(RS)-4-methyl-2-[[(S)-3-methyl-1-(methylcarbamoyl)butyl]carbamoyl]pentyl]phosphinic acid ethyl ester, there was obtained [(R)-1-[[N-[1-[(benzyloxy)carbonyl]-L-prolyl]-D-leucyl]amino]ethyl][(RS)-4-methyl-2-[[(S)-3-methyl-1-(methylcarbamoyl)butyl]carbamoyl]pentyl]phosphinic acid in the form of a white foam;

from [(S)-1-[[N-[1-[(benzyloxy)carbonyl]-L-prolyl]-D-leucyl]amino]ethyl][(RS)-4methyl-2-[[(S)-3-methyl-1-(methylcarbamoyl)butyl]carbamoyl]pentyl]phosphinic acid ethyl ester, there was obtained [(S)-1-[[N-[1-[(benzyloxy)-carbonyl]-L-prolyl]-D-leucyl]amino]ethyl][(RS)-4-methyl-2-[[(S)-3-methyl-1-(methylcarbamoyl)butyl]carbamoyl]- pentyl]phosphinic acid in the form of a white foam;

from [[(S)-3-[1-(benzyloxy)formamido]-2,5-dioxo-1-pyrrolidinyl]methyl][(RS)-4-methyl-2-[[(S)-3-methyl-1-(methylcarbamoyl)butyl]carbamoyl]pentyl]phosphinic acid ethyl ester, there was obtained [[(S)-3-[1-(benzyloxy)formamido]-2,5-dioxo-1-pyrrolidinyl]methyl][(RS)-4-methyl2-[[(S)-3-methyl-1-(methylcarbamoyl)butyl]carbamoyl]pentyl]phosphinic acid in the form of a white foam;

from [[(R)-3-[1-(benzyloxy)formamido]-2,5-dioxo-1-pyrrolidinyl]methyl][(RS)-4-methyl-2-[[(S)-3-methyl-1-(methylcarbamoyl)butyl]carbamoyl]pentyl]phosphinic acid ethyl ester, there was obtained [[(R)-3-[1-(benzyloxy)formamido]-2,5-dioxo-1-pyrrolidinyl]methyl][(RS)-4-methyl-2-[[(S)-3-methyl-1-(methylcarbamoyl)butyl]carbamoyl]pentyl]phosphinic acid in the form of a white foam;

from [[(S)-3[[1-[(benzyloxy)carbonyl]-L-prolyl]amino]-2,5-dioxo-1-pyrrolidinyl]methyl][(RS)-4-methyl-2-[[(S)-3-methyl-1-(methylcarbamoyl)butyl]carbamoyl]pentyl]phosphinic acid ethyl ester, there was obtained [[(S)-3-[[1-[(benzyloxy)carbonyl]-L-prolyl]amino]2,5-dioxo-1-pyrrolidinyl]methyl][(RS)-4-methyl-2-[[(S)-3-methyl-1-(methylcarbamoyl)butyl]carbamoyl]pentyl]phosphinic acid in the form of a white foam;

from [[(R)-3-[[1-[(benzyloxy)carbonyl]-L-prolyl]amino]-2,5-dioxo-1-pyrrolidinyl]methyl][(RS)-4-methyl-2-[[(S)-3-methyl-1-(methylcarbamoyl)butyl]carbamoyl]pentyl]phosphinic acid ethyl ester, there was obtained [[(R)-3-[[1-[(benzyloxy)carbonyl]-L-prolyl]amino]-2,5-dioxo-1-pyrrolidinyl]methyl][(RS)-4-methyl-2-[[(S)-3-methyl-1-(methylcarbamoyl)butyl]carbamoyl]pentyl]phosphinic acid in the form of a white foam;

from [[3,4-dihydro-1,3-dioxonaphth[1,8-cd]azepin-2(1H)-yl]methyl][(RS)-4-methyl -2-[[(S)-3-methyl-1-(methylcarbamoyl)butyl]carbamoyl]pentyl]phosphinic acid ethyl ester, there was obtained [[3,4-dihydro-1,3-dioxonaphth[1,8-cd]azepin-2(1H)-yl]methyl][(RS)-4-methyl-2-[[(S)-3-methyl-1-(methylcarbamoyl)butyl]carbamoyl]pentyl]phosphinic acid in the form of a white foam;

from [[(S)-3-[[1-[(benzyloxy)carbonyl]-L-prolyl]amino]2,6-dioxopiperidino]methyl][(RS)-4-methyl-2-[[(S)-3-methyl-1-(methylcarbamoyl)butyl]carbamoyl]pentyl]phosphinic acid ethyl ester, there was obtained [[(S)-3-[[1-[(benzyloxy)carbonyl]-L-prolyl]amino]-2,6-dioxopiperidino]methyl][(RS)-4-methyl-2-[[(S)-3-methyl-1-(methylcarbamoyl)butyl]carbamoyl]pentyl]phosphinic acid in the form of a white foam;

from [[(R) -3-[[1-[(benzyloxy)carbonyl]-L-prolyl]amino]-2,6-dioxopiperidino]methyl][(RS)-4-methyl-2-[[(S)-3-methyl-1-(methylcarbamoyl)butyl]carbamoyl]pentyl]phosphinic acid ethyl ester, there was obtained [[(R)-3-[[1-[(benzyloxy)carbonyl]-L-prolyl]amino]-2,6-dioxopiperidino]methyl][(RS)-4-methyl-2-[[(S)-3-methyl-1-(methylcarbamoyl)butyl]carbamoyl]pentyl]phosphonic acid in the form of a white foam; and from [(1,3-dihydro-1,3-dioxo-2H-dibenz[e,g]isoindol-2-yl)methyl][(RS)-4-methyl-2-[[(S)-3-methyl-1-(methylcarbamoyl)butyl]carbamoyl]pentyl]phosphinic acid isopropyl ester, there was obtained [(1,3-dihydro-1,3-dioxo-2H-dibenz[e,g]isointol-2-yl)methyl][(RS)-4-methyl-2-[[(S)-3-methyl-1-(methylcarbamoyl)butyl]carbamoyl]pentyl]phosphinic acid in the form of a yellow foam.

EXAMPLE 31

In an analogous manner to that described in Example 25(B), from [(4-chloro-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(4-chloro-1,8-naphthalenedicarboximido)methyl][(RS)-4-methyl-2-[[(S)-3-methyl-1-(methylcarbamoyl)butyl]carbamoyl]pentyl]phosphinic acid in the form of an off-white foam;

from [(RS)-4-methyl-1-[[(S)-3-methyl-1-(methylcarbamoyl)butyl]carbamoyl]pentyl][(1,2-naphthalenedicarboximido)methyl]phosphinic acid ethyl ester, there was obtained [(RS)-4-methyl-1-[[(S)-3-methyl-1-(methylcarbamoyl)butyl]carbamoyl]pentyl][(1,2-naphthalenedicarboximido)methyl]phosphinic acid in the form of an off-white foam;

from [(3-bromo-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(3-bromo-1,8-naphthalenedicarboximido)methyl][(RS)-4-methyl-2-[[(S)-3-methyl-1-(methylcarbamoyl)butyl]carbamoyl]pentyl]phosphinic acid in the form of a white foam;

from [(RS)-4-methyl-2-[[(S)-3-methyl-1-(methylcarbamoyl)butyl]carbamoyl]pentyl][(3-nitro-1,8-naphthalenedicarboximido)methyl]phosphinic acid ethyl ester, there was obtained [(RS)-4-methyl-2-[[(S)-3-methyl-1-(methylcarbamoyl)butyl]carbmoayl]pentyl][(3-nitro-1,8-naphthalenedicarboximido)methyl]phosphinic acid in the form of an off-white foam;

from [(2-methoxy-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(2-methoxy-1,8-naphthalenedicarboximido)methyl][(RS)-4-methyl-2-[[(S)-3-methyl-1-(methylcarbamoyl)butyl]carbamoyl]pentyl]phosphinic acid in the form of an off-white foam;

from [(3,4-dihydro-1,3-dioxo-2(1H)-isoquinolinyl)methyl][(RS)-4-methyl-2-[[(S)-3-methyl-1-(methylcarbamoyl)butyl]carbamoyl]pentyl]phosphinic acid ethyl ester, there was obtained [(3,4-dihydro-1,3-dioxo-2(1H)-isoquinolinyl)methyl][(RS)-4methyl-2-[[(S)-3-methyl-1-(methylcarbamoyl)butyl]carbamoyl]pentyl]phosphinic acid in the form of an off-white foam;

from [(RS)-4-methyl-2-[[(S)-3-methyl-1-(methylcarbamoyl)butyl]carbamoyl]pentyl][[1,3-dioxo-1H-pyrrolo[3,4-c]pyridin-2(3H)-yl]methyl]phosphinic acid ethyl ester, there was obtained [(RS)-4-methyl-2-[[(S)-3-methyl-1-(methylcarbamoyl)butyl]carbamoyl]pentyl][[1,3-dioxo-1H-pyrrolo[3,4-c]pyridin-2(3H)-yl]methyl]phosphinic acid hydrobromide in the form of a yellow foam;

from [[1,3-dioxo-1H-pyrrolo[3,4-b]pyridin-2(3H)-yl]methyl][(RS)-4-methyl-2-[[(S)-3-methyl-1-(methylcarbamoyl)butyl]carbamoyl]pentyl]phosphinic acid ethyl ester, there was obtained [[1,3-dioxo-1H-pyrrolo[3,4-b]pyridin-2(3H)-yl]methyl][(RS)-4-methyl-2-[[(S)-3-methyl-1-(methylcarbamoyl)butyl]carbamoyl]pentyl]phosphinic acid in the form of a yellow-brown foam; and from [(4-methoxy-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(4-methoxy-1,8-naphthalenedicarboximido)methyl][(RS)-4-methyl-2-[[(S)-3-methyl-1-(methylcarbamoyl)butyl]carbamoyl]pentyl]phosphinic acid in the form of a pale yellow foam.

EXAMPLE 32

In an analogous manner to that described in Example 28(B), from [(4-acetamido-1,8-naphthalenedicarboximido)methyl][(RS)-4-methyl-2-[[(S)-3-methyl-1-(methylcarbamoyl)butyl]carbamoyl]pentyl]phosphinic acid ethyl ester, there was obtained [(4-acetamido-1,8-naphthalenedicarboximido)methyl][(RS)-4-methyl-2-[[(S)-3-methyl-1-(methylcarbamoyl)butyl]carbamoyl]pentyl]phosphinic acid in the form of a yellow-green foam.

EXAMPLE 33

In analogous manner to that described in Example 1(B), from [[(S)-3-acetamidosuccinimido]methyl][(RS)-4-methyl-2-[[(S)-3-methyl-1-(methylcarbamoyl)butyl]carbamoyl]pentyl]phosphinic acid ethyl ester, there was obtained [[(S)-3-acetamidosuccinimido]methyl][(RS)-4-methyl-2-[[(S)-3-methyl-1-(methylcarbamoyl)butyl]carbamoyl]pentyl]phosphinic acid in the form of a white foam; and from [[(R)-3-acetamidosuccinimido]methyl][(RS)-4-methyl-2-[[(S)-3-methyl-1-(methylcarbamoyl)butyl]carbamoyl]pentyl]phosphinic acid ethyl ester, there was obtained [[(R)-3-acetamidosuccinimido]methyl][(RS)-4-methyl-2-[[(S)-3-methyl-1-(methylcarbamoyl)butyl]carbamoyl]pentyl]phosphinic acid in the form of a white foam.

EXAMPLE 34

A solution of 0.2 g of [(4-amino-1,8-naphthalenedicarboximido)methyl][(RS)-4-methyl-2-[[(S)-3-methyl-1-(methylcarbamoyl)butyl]carbamoyl]pentyl]phosphinic acid in 2 ml of glacial acetic acid was treated with two drops of bromine. The solution was stirred at room temperature for 30 minutes and then evaporated under reduced pressure. After an additional four evaporations from 10 ml of methanol each time there were obtained 230 mg of [(4-amino-3-bromo-1,8-naphthalenedicarboximido)methyl][(RS)-4-methyl-2-[[(S)-3-methyl-1-(methylcarbamoyl)butyl]carbamoyl]pentyl]phosphinic acid in the form of a yellow powder.

EXAMPLE 35

A solution of 0.075 g of [(4-hydroxy-1,8-naphthalenedicarboximido)methyl][(RS)-4-methyl-2-[[(S)-3-methyl-1-(methylcarbamoyl)butyl]carbamoyl]phenyl]phosphinic acid in 17 ml of glacial acetic acid was treated with 10 drops of bromine and the mixture was left to stand at room temperature for 3 days. The solvent was then removed by evaporation and the residue was treated with 20 ml of toluene and re-evaporated. This procedure was repeated 5 times and the product was finally taken up in 20 ml of methanol/dichloromethane (1:1) and re-evaporated to give 0.085 g of [(3-bromo-4-hydroxy-1,8-naphthalenedicarboximido)methyl][(RS)-4-methyl-2-[[(S)-3-methyl-1-(methylcarbamoyl)butyl]carbamoyl]phenyl]phosphinic acid in the form of a yellow foam.

EXAMPLE 36

(A) The Preparation of the Starting Material (i) In a manner analogous to that described in Example 9(A)(i) and (ii), but starting with (aminomethyl)[(RS)-4-methyl-2-[[(S)-3-methyl-1-(methylcarbamoyl)butyl]carbamoyl]pentyl]phosphinic acid ethyl ester acetate [prepared as described in Example 20(A)-(iii)], there was obtained benzyl(S)-2-[[(S)-1-[[[ethoxy[(RS)-4-methyl-2-[[(S)-3-methyl-1-(methylcarbamoyl)butyl]carbamoyl]pentyl]phosphinyl]methyl]carbamoyl]-3-methylbutyl]carbamoyl]-1-pyrrolidinecarboxylate in the form of a white foam.

(ii) 0.36 g of benzyl(S)-2-[[(S)-1-[[[ethoxy[(RS)-4-methyl-2-[[(S)-3-methyl-1-(methylcarbamoyl)butyl]carbamoyl]pentyl]phosphinyl]methyl]carbamoyl]-3-methylbutyl]carbamoyl]-1-pyrrolidinecarboxylate was dissolved in 5 ml of ethanol containing 0.5 ml of 1M hydrochloric acid. The solution was hydrogenated over 5% palladium-on-charcoal for 2 hours. After filtration and evaporation of the filtrate, the residue was re-evaporated with toluene until a white solid was obtained. This solid was dissolved in 6 ml of dichloromethane. The solution was cooled to 0° C. and treated with 0.15 ml of triethylamine and 0.064 ml of benzoyl chloride. The mixture was stirred at room temperature for 16 hours and the solvent was then removed by evaporation. The residue was dissolved in ethyl acetate. The mixture was filtered and the filtrate was evaporated to give a pale yellow gum. Chromatography on silica gel using 3% ethanol in chloroform for the elution followed by evaporation yielded 0.32 g of [[[N-(1-benzoyl-L-prolyl)-L-leucyl]amino]methyl][(RS)-4-methyl-2-[[(S)-3-methyl-1-methylcarbamoyl)butyl]carbamoyl]pentyl]phosphinic acid ethyl ester in the form of a white foam.

(B) The Process 0.25 g of [[[N-(1-benzoyl-L-prolyl)-L-leucyl]amino]methyl][(RS)-4-methyl-2-[[(S)-3-methyl-1-(methylcarbamoyl)butyl]carbamoyl]pentyl]phosphinic acid ethyl ester was dissolved in a mixture of 1 ml of acetic acid and 1 ml of 45% hydrogen bromide in acetic acid and the mixture was left to stand at room temperature overnight. The solution was treated with diethyl ether. The precipitated gum was allowed to settle and the ethereal solution was removed by decantation. Further treatment with diethyl ether followed by dichloromethane and subsequent drying in a high vacuum yielded 0.17 g of [[[(N-(1-benzoyl-L-prolyl)-L-leucyl]amino]methyl][(RS)-4-methyl-2-[[(S)-3-methyl-1-(methylcarbamoyl)butyl]carbamoyl]pentyl]phosphinic acid in the form of a light brown foam containing some hydrogen bromide.

EXAMPLE 37

(A) The Preparation of the Stating Material

In a manner analogous to tht described in Example 36(A), but using trifluoroacetic anhydride in place of benzoyl chloride, there was obtained [(RS)-4-methyl-2-[[(S)-3-methyl-1-(methylcarbamoyl)butyl]carbamoyl]pentyl][[[N-[1-trifluoroacetyl)-L-prolyl]-L-leucyl]amino]methyl]phosphinic acid ethyl ester in the form of a pale yellow foam.

(B) The Process

[(RS)-4-methyl-2-[[(S)-3-methyl-1-(methylcarbamoyl)butyl]carbamoyl]pentyl][[[N-[1-trifluoroacetyl)-L-prolyl]-L-leucyl]amino]methyl]phosphinic acid ethyl ester was treated in a manner analogous to that described in Example 36(B) to give [(RS)-4-methyl-2-[[(S)-3-methyl-1-(methylcarbamoyl)butyl]carbamoyl]pentyl][[[N-[1-trifluoroacetyl)-L-prolyl]-L-leucyl]amino]methyl]phosphinic acid in the form of a pale brown solid containing some hydrogen bromide.

EXAMPLE 38

(A) The Preparation of the Starting Material 0.65 g of [[[N-[1-[(benzyloxy)carbonyl]-L-prolyl]-L-leucyl]amino]methyl][(RS)-4-methyl-2-[[(S)-3-methyl-1-(methylcarbamoyl)butyl]carbamoyl]pentyl]phosphinic acid ethyl ester was dissolved in 8 ml of acetic acid. Thereafter, 2 ml of acetaldehyde were added and the mixture was hydrogenated for 4 hours over 0.01 g of 5% palladium-on-charcoal. The solution was filtered and the filtrate was evaporated to dryness.

(B) The Process

The product obtained according to paragraph (a) was dissolved in 2 ml of 45% hydrogen bromide in acetic acid and left to stand at room temperature overnight. The solution was evaporated and the residue was re-evaporated with toluene until a pale brown solid was obtained. This solid (0.6 g) was precipitated from methanolic solution by the addition of diethyl ether and was then dried in a high vacuum to yield [[[N-(1-ethyl-L-prolyl)-L-leucyl]amino]methyl][(RS)-4-methyl-2-[[(S)-3-methyl-1-(methylcarbamoyl)butyl]carbamoyl]pentyl]phosphinic acid in the form of a brown foam.

EXAMPLE 39

0.55 g of [(RS)-4-methyl-2-[[(S)-3-methyl-1-(methylcarbamoyl)butyl]carbamoyl]pentyl][[(N-L-prolyl-L-leucyl)amino]methyl]phosphinic acid ethyl ester was dissolved in 4 ml of acetic acid and 2 ml of 45% hydrogen bromide in acetic acid and the mixture was left to stand at room temperature overnight. The solvent was removed by evaporation and the residue was re-evaporated with toluene to give 0.47 g of a pale brown foam. Precipitation from methanolic solution by the addition of diethyl ether and drying in a high vacuum yielded [(RS)-4-methyl-2-[[(S)-3-methyl-1-(methylcarbamoyl)butyl]carbamoyl]pentyl][[(N-L-prolyl-L-leucyl)amino]methyl]phosphinic acid in the form of a brown foam.

EXAMPLE 40

(A) The Preparation of Starting Material

In a manner analagous to that described in Example 9(A)(i) und (ii), but starting with (aminomethyl)[(RS)-4-methyl-2-[[(S)-3-methyl-1-(methylcarbamoyl)butyl]carbamoyl]pentyl]phosphinic acid ethyl ester and using $N^2$-[(benzyloxy)carbonyl]-$N^6$-phthaloyl-L-lysine in place of N-[(benzyloxy)carbonyl]-L-proline, there was obtained [[[N-[(S)-2-[1-(benzyloxy)formamido]-6-phthalimidohexanoyl]-L-leucyl]amino]methyl][(RS-4-methyl-2-[[(S)-3-methyl-1-(methylcarbamoyl)butyl]carbamoyl]pentyl]phosphinic acid ethyl ester in the form of a white foam.

(B) The Process 0.6 g of [[[N-[(S)-2-[1-(benzyloxy)formamido]-6-phthalimidohexanoyl]-L-leucyl]amino]methyl][RS-4-methyl-2-[[(S)-3-methyl-1-(methylcarbamoyl)butyl]carbamoyl]pentyl]phosphinic acid ethyl ester was dissolved in 2 ml of acetic acid and 2 ml of 45% hydrogen bromide in acetic acid and left to stand at room temperature overnight. The solvent was removed by evaporation and the residue was re-evaporated with toluene until a solid was obtained. This solid was dissolved in aqueous potassium hydrogen carbonate solution, 0.14 ml of benzyl chloroformate was added and the mixture was stirred for 4 hours. The solution was extracted twice with diethyl ether and acidified with hydrochloric acid. The solid was separated and dissolved by extraction with hot chloroform. The organic solution was dried over anhydrous magnesium sulfate and evaporated to yield 0.53 g of [[[N-[(S)-2-[1-(benzyloxy)formamido]-6-phthalimidohexanoyl]-L-leucyl]amino]methyl][(RS)-4-methyl-2-[[(S)-3-methyl-1-(methylcarbamoyl)butyl]carbamoyl]pentyl]phosphinic acid in the form of an amorphous cream powder.

EXAMPLE 41

In a manner analogous to that described in Example 39, there was obtained [[[N-[N-[(benzyloxy)carbonyl]-L-alanyl]-L-leucyl]amino]methyl][(RS)-4-methyl-2-[[(S)-3-methyl-1-(methylcarbamoyl)butyl]carbamoyl]-pentyl]phosphinic acid in the form of a pale brown powder.

EXAMPLE 42

(A) The Preparation of the Starting Material

In a manner analogous to that described in Example 36(A)(i), but using N-(benzyloxy)carbonyl-L-alanine in place of N-(benzyloxy)carbonyl-L-leucine, there was obtained [[[N-[1-[(benzyloxy)carbonyl]-L-prolyl]-L-alanyl]amino]methyl][(RS)-4-methyl-2-[[(S)-3-methyl-1-(methylcarbamoyl)butyl]carbamoyl]pentyl]phosphinic acid ethyl ester in the form of a foam.

(B) The Process

[[[N-[1-[(benzyloxy)carbonyl]-L-prolyl]-L-alanyl]amino]methyl][(RS)-4-methyl-2-[[(S)-3-methyl-1-(methylcarbamoyl)butyl]carbamoyl]pentyl]phosphinic acid ethyl ester was treated in a similar manner to that described in Example 39(B) to yield [[[N-[1-[(benzyloxy)carbonyl]-L-prolyl]-L-alanyl]amino]methyl][(RS)-4-methyl-2-[[(S)-3-methyl-1-(methylcarbamoyl)butyl]carbamoyl]pentyl]phosphinic acid in the form of a white foam.

EXAMPLE 43

(A) The Preparation of the Starting Material

In a manner analogous to that described in Example 41(A) there was obtained [[[(S)-2-[1-(benzyloxy)carbonyl]-L-prolyl]amino]-6-phthalimidohexanamido]methyl][(RS)-4-methyl-2-[[(S)-3-methyl-1-(methylcarbamoyl)butyl]carbamoyl]pentyl]phosphinic acid ethyl ester.

(B) The Process

[[[(S)-2-[1-(benzyloxy)carbonyl]-L-prolyl]amino]-6-phthalimidohexanamido]methyl][(RS)-4-methyl-2-[[(S)-3-methyl-1-(methylcarbamoyl)butyl]carbamoyl]pentyl]phosphinic acid ethyl ester was treated in a similar manner to that described in Example 39(B) to give [[[(S)-2-[1-(benzyloxy)carbonyl]-L- prolyl]amino]-6-phthalimidohexanamido]methyl][(RS)-4-methyl-2-[[(S)-3-methyl-1-(methylcarbamoyl)butyl]carbamoyl]pentyl]phosphinic acid in the form of a foam.

EXAMPLE 44

(A) The Preparation of the Starting Material (i) 21.0 g of $N^6$-[(benzyloxy)carbonyl]-L-lysine were dissolved in 75 ml of 2M sodium hydroxide solution and 75 ml of dioxane. Thereafter, 18.0 g of di-tert.butyl dicarbonate were added and the mixture was stirred at room temperature for 16 hours. The solution was evaporated in order to remove dioxane, water was added, the solution was extracted with diethyl ether and acidified with 6M hydrochloroic acid. The product was taken up in ethyl acetate, washed with sodium chloride solution, dried over magnesium sulfate and evaporated to give an oil. A solution of this oil in tetrahydrofuran was cooled to −15° C. and treated with 8.51 ml of N-ethylmorpholine, 8.61 ml of isobutylchloroformate and, after 5 minutes, with 10.0 ml of a 40% aqueous solution of methylamine. After stirring at 0° C. for 2 hours, the solvent was removed by evaporation and the residue was dissolved in ethyl acetate. The organic solution was washed with water, 5% citric acid solution, water, 5% sodium hydrogen carbonate solution and sodium chloride solution, dried over anhydrous magnesium sulfate and evaporated. Recrystallization from ethyl acetate yielded 20.5 g of $N^6$-[(benzyloxy)carbonyl]-$N^2$-(tert.-butoxycarbonyl)-L-lysine methylamide in the form of a white solid of melting point 100°–102° C.

(ii) 5.7 g of (R or S)-2-[[ethoxy(phthalimidomethyl)phosphinyl]methyl]-4-methylvaleric acid were dissolved in tetrahydrofuran and cooled to −20° C. Thereafter, 1.90 ml of N-ethylmorpholine and 1.97 ml of isobutyl chloroformate were added and, after stirring at −20° C. for 20 minutes, 2.4 g of N-hydroxybenzotriazole were added. The mixture was then stirred at −20° C. for 20 minutes. A solution of $N^6$-[(benzyloxy)carbonyl]-L-lysine methylamide hydrochloride (prepared by treating 5.91 g of $N^6$[(benzyloxy)carbonyl]-$N^2$-(tert.-butoxycarbonyl)-L-lysine methylamide with 4M hydrogen chloride in dioxane for 30 minutes at room temperature followed by evaporation and trituration with diethyl ether) in dimethylformamide was neutralized with 1.90 ml of N-ethylmorpholine and added to the mixed anhydride solution prepared as described above. The mixture was stirred at 0° C. for 1 hour, left to stand at room temperature overnight and then evaporated. The residue was taken up in dichloromethane, washed with water, 1M hydrochloric acid, water, 5% sodium hydrogen carbonate solution and sodium chloride solution, dried over anhydrous magnesium sulfate and evaporated to give an oil. Chromatography on silica gel using 4% methanol in chloroform for the elution yielded 6.8 g of benzyl [(S)-5-[(R or S)-2-[[ethoxy(phthalimidomethyl)phosphinyl]methyl]-4-methylvalerimido]-5-(methylcarbamoyl)pentyl]carbamate in the form of an oil.

(iii) 6.56 g of benzyl [(S)-5-[(R or S)-2-[[ethoxy(phthalimidomethyl)phosphinyl]methyl]-4-methylvalerimido]-5-(methylcarbamoyl)pentyl]carbamate were dissolved in a mixture of 120 ml of ethanol and 1.96 ml of hydrazine hydrate, the mixture was stirred for 16 hours and then evaporated. Traces of hydrazine hydrate were removed by the addition and evaporation of ethanol followed by toluene. The residue was suspended in dichloromethane and acidified with acetic acid. The mixture was stirred at room temperature for 30 minutes, filtered and the filtrate was evaporated. The residue was taken up in 5% citric acid solution, extracted with diethyl ether and filtered. The filtrate was made basic by the addition of solid sodium hydrogen carbonate and the product was extracted three times with 20 ml of dichloromethane each time. The solution was dried over magnesium sulfate and evaporated to 20 ml, 2.82 g of 1,8-naphthalic anhydride were added and the solution was stirred at room temperature for 16 hours. Thereafter, 1.17 g of N-hydroxybenzotriazole and 1.61 g of N,N'-dicyclohexylcarbodiimide were added to the solution at 0° C. The solution was stirred at 0° C. for 2 hours and filtered. The filtrate was washed with 5% sodium hydrogen carbonate solution, dried over anhydrous magnesium sulfate and evaporated to give an oil. Chromatography on silica gel using 4% methanol in dichloromethane for the elution yielded 4.0 g of benzyl [(S)-5-[(R or S)-2-[[ethoxy[(1,8-naphthalenedicarboximido)methyl]phosphinyl]methyl]-4-methylvaleramido]-5-(ethylcarbamoyl)pentyl]carbamate in the form of a white foam.

(iv) 1.0 g of benzyl [(S)-5-[(R or S)-2-[[ethoxy[(1,8-naphthalenedicarboximido)methyl]phosphinyl]methyl]-4-methylvaleramido]-5-(ethylcarbamoyl)pentyl]carbamate in ethanol containing 1.4 ml of 1M hydrochloric acid was hydrogenated for 5 hours over 5% palladium-on-charcoal. The catalyst was removed by filtration and the filtrate was evaporated to dryness. Final traces of ethanol were removed by 2-fold re-evaporation with 15 ml of toluene each time. The residue was taken up in dichloromethane, cooled to 0° C., neutralized with 0.18 ml of N-ethylmorpholine and treated with 0.293 g of N-[(benzyloxy)carbonyl]-glycine, 0.227 g of hydroxybenzotriazole and 0.316 g of N,N'-dicyclohexylcarbodiimide. The mixture was stirred at 0° C. for 1 hour, left to stand at 4° C. overnight and filtered. The filtrate was washed with 5% citric acid, water, 5% sodium hydrogen carbonate solution and sodium chloride solution, dried over anhydrous magnesium sulfate and evaporated. Chromatography on silica gel using 7.5% methanol in ethyl acetate for the elution yielded 0.51 g of benzyl [[[(S)-5-[(R or S)-2-[[ethoxy[(1,8-naphthalenedicarboximido)methyl]phosphinyl]methyl]-4-methylvaleramido]-5-(methylcarbamoyl)pentyl]carbamoyl]methyl]carbamate in the form of a foam.

(B) THE PROCESS 0.1 g of benzyl [[[(S)-5-[(R or S)-2-[[ethoxy[(1,8-naphthalenedicarboximido)methyl]phosphinyl]methyl]-4-methylvaleramido]-5-(methylcarbamoyl)pentyl]carbamoyl]methyl]carbamate in 3 ml of 45% hydrogen bromide in acetic acid was left to stand at room temperature for 16 hours. The mixture was evaporated and the residue was re-evaporated three times with 10 ml of toluene each time. Precipitation from methanol/diethyl ether followed by lyophilization from water yielded 0.11 g of [(R or S)-2-[[(S)-5-(glycylamino)-1-(methylcarbamoyl)pentyl]carbamoyl]-4-methylpentyl][(1,8-naphthalenedicarboximido)methyl]phosphinic acid hydrobromide in the form of a white freeze dried solid.

The (R or S)-2-[[(ethoxy)(phthalimidomethyl)phosphinyl]methyl]-4-methylvaleric acid used in paragraph (A) (ii) was prepared as follows (a) A vigorously stirred mixture of 17.6 g (0.27 mol) of crystalline phosphinic acid and 43.6 g (0.2 mol) of benzyl 2-isobutylacrylate in 400 ml of dichloromethane was cooled to 0° C. and treated dropwise with 53.4 g (0.53 mol) of triethylamine while maintaining the temperature at below 5° C. After completion of the addition, a solution of 56.0 g (0.52 mol) of trimethylsilyl chloride in 100 ml of dichloromethane was added while stirring vigorously and maintaining the temperature at 10°-12° C. After 30 minutes, the cooling bath was removed and the mixture was stirred at room temperature for 24 hours. The mixture was then treated with 200 ml of water and 30 ml of 10% sulfuric acid. The organic phase was separated and washed with 200 ml of saturated sodium chloride solution. The combined aqueous extracts were re-extracted with 100 ml of dichloromethane and the organic phase was washed with 100 ml of sodium chloride solution and added to the previously obtained dichloromethane extracts. After drying over anhydrous sodium sulfate, the dichloromethane was removed by evaporation to give 59.2 g of [(RS)-2-[(benzyloxy)carbonyl]-4-methylpentyl]phosphinic acid in the form of a colorless oil. (b) The compound prepared in the preceding paragraph was dissolved in 600 ml of ethyl acetate. Thereafter, 25.0 g of S(−)-α-methylbenzylamine were added and the solution was left to crystallize for 24 hours. The crystalline salt was collected by filtration and dried to give 34.0 g of a white solid which was recrystallized overnight from a mixture of 120 ml of ethanol and 48 ml of ethyl acetate. The solid was collected and dried to give 21.3 g of a crystalline salt which was recrystallized overnight from a mixture of 120 ml of ethanol and ethyl acetate. There were obtained 16.8 g of [(R or S)-2-[benzyloxy)carbonyl]-4-methylpentyl]phosphinic acid S(−)-α-methylbenzylamine salt in the form of white crystals of melting point 137°–138° C. and [α]20/589=−8.9° (c=5% in ethanol).

(c) A suspension of 5.8 g of the salt prepared as described in the preceding paragraph in 100 ml of ethyl acetate was shaken with 100 ml of 10% sulfuric acid until a clear solution was obtained. The organic layer was separated, washed with 100 ml of saturated sodium chloride solution and dried over anhydrous sodium sulfate. After evaporation, there were obtained 4.0 g of [(R or S)-2-[benzyloxy)carbonyl]-4-methylpentyl]phosphinic acid in the form of a colorless oil; [α]20/589=−12.3° (c =5% in ethanol).

(d) 4.0 g of the compound prepared in the preceding paragraph were dissolved in 40 ml of dry tetrahydrofuran containing 0.7 ml of ethanol. 3.1 g of N,N'-dicyclohexylcarbodiimide and 0.17 g of 4-dimethylaminopyridine were added and the mixture was stirred at room temperature for 18 hours. The solvent was then removed by evaporation. The residue was triturated with 50 ml of ethyl acetate and the dicyclohexylurea was removed by filtration. The filtrate was washed with 50 ml of 5% potassium hydrogen sulfate solution and then with 50 ml of saturated sodium hydrogen carbonate solution. After drying over anhydrous sodium sulfate, the ethyl acetate was removed by evaporation to give 4.5 g of benzyl (R or S)-2-[(ethoxyphosphinyl)methyl]-4-methylvalerate in the form of a colorless oil; [α]20/589=−8.5° (c=5% in ethanol.

(e) A mixture of 4.5 g of benzyl (R or S)-2-[(ethoxyphosphinyl)methyl]-4-methylvalerate and 1.8 g of diisopropylethylamine in 30 ml of dichloromethane was cooled in an ice-bath while stirring under nitrogen. Seven (7) ml of bis(trimethylsilyl) acetamide were added. The mixture was stirred for 5 minutes and then 3.36 g of N-bromomethylphthalimide were added. The cooling bath was removed and the mixture was left to reach room temperature. After stirring for an additional 5 hours, the solution was washed with 50 ml of 10% sulfuric acid and 50 ml of sodium chloride solution, dried over anhydrous sodium sulfate and evaporated to give 6.6 g of a yellow oil which was purified by flash chromatography on silica gel using ethyl acetate/n-hexane (3:1) for the elution. There were obtained 4.5 g of benzyl (R or S)-2-[[(ethoxy)(phthalimidomethyl)phosphinyl]methyl]-4-methylvalerate in the form of a colorless oil.

(f) 4.5 g of benzyl (R or S)-2-[[(ethoxy)(phthalimidomethyl)phosphinyl]methyl]-4-methylvalerate were dissolved in 120 ml of ethanol and the solution was hydrogenated over 1.6 g of 10% palladium-on-charcoal for 5.5 hours. After filtration and evaporation of the filtrate, there were obtained 3.0 g of (R or S)-2-[[(ethoxy)(phthalimidomethyl)phosphinyl]methyl]-4-methylvaleric acid in the form of A white foam.

The following Examples illustrate pharmaceutical preparations containing the compounds of formula I provided by the invention:

EXAMPLE A

Tablets containing the following ingredients may be produced in a conventional manner:

| Ingredient | Per tablet |
|---|---|
| [(3-Aminophthalimido)methyl][(RS)-4-methyl-2-[[(S)-3-methyl-1-(methylcarbamoyl)butyl]carbamoyl]pentyl]phosphinic acid | 10.0 mg |
| Lactose | 125.0 mg |
| Maize starch | 75.0 mg |
| Talc | 4.0 mg |
| Magnesium stearate | 1.0 mg |
| Tablet weight | 215.0 mg |

EXAMPLE B

Capsules containing the following ingredients may be produced in a conventional manner:

| Ingredient | Per capsule |
|---|---|
| [(3-Aminophthalimido)methyl][(RS)-4-methyl-2-[[(S)-3-methyl-1-(methylcarbamoyl)butyl]carbamoyl]pentyl]phosphinic acid | 10.0 mg |
| Lactose | 165.0 mg |
| Maize starch | 20.0 mg |
| Talc | 5.0 mg |
| Capsule fill weight | 200.0 mg |

We claim:
1. A compound of the formula

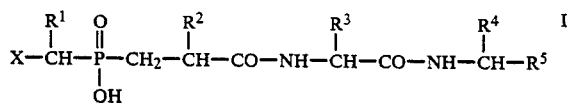

wherein
$R^1$ is a hydrogen, $C_1-C_6$-alkyl or phenyl-($C_1-C_6$-alkyl wherein phenyl is unsubstituted or substituted with one or more substituents selected from $C_1-C_6$-alkyl, $C_1-C_6$-alkoxy, halogen or trifluoromethyl;
$R^2$ is a $C_2-C_5$-alkyl;
$R^3$ is isopropyl, isobutyl, benzyl, p-hydroxybenzyl, hydroxymethyl, mercaptomethyl, 1-hydroxyethyl, 2-methylthioethyl, carboxymethyl, 2-carboxyethyl, 3-quanidinopropyl or aminobutyl, wherein a hydroxy group can be protected by a tert-butylbenzyl, tetrahydropyranyl or acetyl group, a mercapto group can be protected by a tert-butyl or benzyl group, an amino group can be acylated by a tert. butoxycarbonyl, benzyloxycarbonyl, formyl, trityl, trifluoroacetyl, 2-(biphenylyl)isopropoxycarbonyl or isobornyloxycarbonyl group, or can be sulfonylated by a $C_1-C_6$-alkane-sulfonyl, benzenesulfonyl or p-toluenesulfonyl group, and a carboxyl group can be amidated to an aminocarbonyl, ($C_1-C_6$-alkyl)aminocarbonyl, di($C_1-C_6$-alkyl)aminocarbonyl or phenylaminocarbonyl;
$R^4$ is a hydrogen or methyl; or
$R^3$ and $R^4$ taken together are a group of the formula $-(CH_2)_n-$ in which n is an integer from 4 to 11 inclusive;
$R^5$ is a hydrogen, $C_1-C_6$-alkyl, carboxyl, $C_1-C_6$-alkoxycarbonyl or $C_1-C_6$-alkylaminocarbonyl; and
X is either c cyclic imido group of the formula

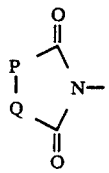

wherein
P and Q taken together are a group of the formula $-CH(R')-CH(R')-$, $-CH(R')-CH(R')-CH(R')-$, $-O-CH(R')-$, $-N(R')-CH(R')-$, $-N(R')-N(R')-$, $-N=N-$ or $-C(R')=C(R')-$ in which each
R' is a hydrogen; $C_1-C_6$-alkyl; phenyl unsubstituted or substituted with one or more substituents selected form $C_1-C_6$-alkyl, $C_1-C_6$-alkoxy, halogen or trifluoromethyl; phenyl-($C_1-C_6$-alkyl) wherein phenyl is unsubstituted or substituted with one or more substituents selected from $C_1-C_6$-alkyl, $C_1-C_6$-alkoxy, halogen or trifluoromethyl; $C_1-C_6$-alkanoylamino; or an acylamino group of the formula $H_2N-CH(-R)-CONH-$ wherein R is isopropyl, isobutyl, benzyl, p-hydroxybenzyl, hydroxymethyl, mercaptomethyl, 1-hydroxyethyl, 2-methylthioethyl, carboxymethyl, 2-carboxyethyl, 3-quanidinopropyl or aminobutyl, in which the amino group can be protected by a tert. butoxycarbonyl, benzyloxycarbonyl, formyl, trityl, trifluoroacetyl, 2-(biphenylyl)-isopropoxycarbonyl or isobornyloxycarbonyl group, or
P and Q taken together are unsubstituted 1,2-phenylene, thienylene, 1,2-naphthylene, 2,3-naphthylene, 1,8-naphthylene or 2,3-anthrylene or substituted by one or more substituents selected from $C_1-C_6$-alkyl, $C_1-C_6$-alkoxy, halogen, hydroxy, phenyl-($C_1-C_6$-alkoxy) wherein phenyl is unsubstituted or substituted with one or more substituents selected from $C_1-C_6$-alkyl, $C^1-C^6$-alkoxy, halogen or trifluoromethyl, nitro, amino, $C_1-C_6$-alkanoyl-amino, mono($C_1-C_6$-alkyl)amino, di($C_1-C_6$-alkyl)-amino and $C_1-C_6$-alkylsulfonylamino; or a group of the formula

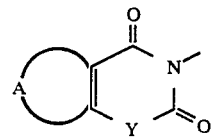

wherein
A is a residue of benzene, napthalene or enthracene which is unsubstituted or substituted by one or more substituents selected from $C_1-C_6$-alkyl, $C_1-C_6$-alkoxy, halogen, hydroxy, phenyl-($C_1-C_6$-alkoxy)

wherein phenyl is unsubstituted or substituted with one or more substituents selected from $C_1$–$C_6$-alkyl, $C_1$–$C_6$-alkoxy, halogen or trifluoromethyl, nitro, amino, $C_1$–$C_6$-alkanoyl-amino, mono ($C_1$–$C_6$-alkyl)amino, di($C_1$–$C_6$-alkyl)-amino and $C_1$–$C_6$-alkylsulfonylamino and Y is -O-, -NH- or NR$^q$ in which R$^q$ is hydrogen or $C_1$–$C_6$-alkyl, or a group of the formula

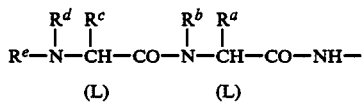

(a)

Ra is isopropyl, isobutyl, benzyl, p-hydroxybenzyl, hydroxymethyl, mercaptomethyl, 1-hydroxyethyl, 2-methylthioethyl, carboxymethyl, 2-carboxyethyl, 3-quanidinopropyl or aminobutyl, wherein a hydroxy group can be protected by a tert-butyl benzyl, tetrahydropyranyl or acetyl group, a mercapto group can be protected by a tert-butyl or benzyl group, an amino group can be acylated by a tert. butoxycarbonyl, benzyloxycarbonyl, formyl, trityl, trifluoroacetyl, 2-(biphenylyl)isopropoxycarbonyl or isobornyloxycarbonyl group, or can be sulfonylated by a $C_1$–$C_6$-alkane-sulfonyl, benzenesulfonyl or p-toluenesulfonyl group, and a carboxyl group can be amidated to an aminocarbonyl, ($C_1$–$C_6$-alkyl)aminocarbonyl, di($C_1$–$C_6$-alkyl)-amino-carbonyl or phenylaminocarbonyl, R$^b$ is hydrogen or R$^a$ and R$^b$ taken together are trimethylene, R$^c$ is isopropyl, isobutyl, benzyl, p-hydroxybenzyl, hydroxymethyl, mercaptomethyl, 1-hydroxyethyl, 2-methylthioethyl, carboxymethyl, 2-carboxyethyl, 3-quanidinopropyl or aminobutyl, wherein a hydroxy group can be protected by a tert-butyl benzyl, tetrahydropyranyl or acetyl group, a mercapto group can be protected by a tert-butyl or benzyl group, an amino group can be acylated by a tert. butoxycarbonyl, benzyloxycarbonyl, formyl, trityl, trifluoroacetyl, 2-(biphenylyl)isopropoxycarbonyl or isobornyloxycarbonyl group, or can be sulfonylated by a $C_1$–$C_6$-alkane-sulfonyl, benzenesulfonyl or p-toluenesulfonyl group, and a carboxyl group can be amidated to an aminocarbonyl, ($C_1$–$C_6$-alkyl)-aminocarbonyl, di($C_1$–$C_6$-alkyl)amino-carbonyl or phenylaminocarbonyl, R$^d$ is hydrogen or R$^c$ and R$^d$ taken together are trimethylene and R$^e$ is a protecting group selected from tert. butoxycarbonyl, benzyloxycarbonlyl, formyl, trityl, trifluoroacetyl, 2-(biphenylyl)-isopropoxycarbonyl or isobornyloxycarbonyl, acyl is derived from a $C_1$–$C_6$-alkanoic acid or a phenyl-($C_1$–$C_6$-alkanoic) acid wherein phenyl is unsubstituted or substituted with one or more substituents selected from $C_1$–$C_6$-alkyl, $C_1$–$C_6$-alkoxy, halogen or trifluoromethyl, $C_1$–$C_6$-alkyl-sulfonyl or phenylsulfonyl wherein phenyl is unsubstituted or substituted with one or more substituents selected from $C_1$–$C_6$-alkyl, $C_1$–$C_6$-alkoxy, halogen or trifluoromethyl, or a pharmaceutically acceptable salt thereof.

2. A compound according to claim 1, wherein $R^1$ is hydrogen or $C_1$–$C_6$-alkyl.

3. A compound according to claim 2, wherein $R^1$ is hydrogen or a methyl.

4. A compound according to claim 2, wherein $R^2$ is $C_3$- or $C_4$-alkyl.

5. A compound according to claim 3, wherein $R^2$ is n-propyl, isobutyl or sec-butyl.

6. A compound according to claim 4, wherein $R^3$ is isobutyl, $R^4$ is hydrogen or $R^3$ and $R^4$ taken together are a group of the formula —$(CH_2)_n$— in which n stands for an integer from 5 to 9 inclusive and $R^5$ is hydrogen.

7. A compound according to claim 5, wherein $R^3$ is isobutyl, $R^4$ is methyl and $R^5$ is carboxyl or $C_1$–$C_6$-alkoxycarbonyl.

8. A compound according to claim 7, wherein $R^5$ is carboxyl or ethoxycarbonyl.

9. A compound according to claim 6, wherein X is a cyclic imido group of the formula

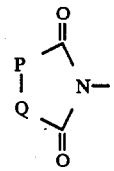

(b)

wherein P and Q taken together are a group of the formula

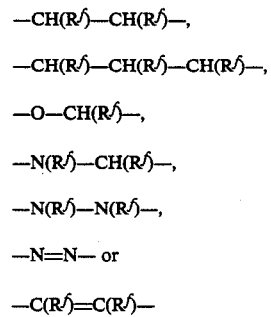

wherein each R$^f$ is a hydrogen; $C_1$–$C_6$-alkyl; phenyl unsubstituted or substituted with one or more substituents selected from $C_1$–$C_6$-alkyl, $C_1$–$C_6$-alkoxy, halogen or trifluoromethyl; phenyl -( $C_1$–$C_6$-alkyl) wherein phenyl is unsubstituted or substituted with one or more substituents selected from $C_1$–$C_6$-alkyl, $C_1$–$C_6$-alkoxy, halogen or trifluoromethyl; $C_1$–$C_6$-alkanoylamino; or an acylamino group of the formula $H_2N$—CH(-R)—CONH—wherein R is isopropyl, isobutyl, benzyl, p-hydroxybenzyl, hydroxymethyl, mercaptomethyl, 1-hydroxyethyl, 2-methylthioethyl, carboxymethyl, 2-carboxyethyl, 3-quanidinopropyl or aminobutyl, in which the amino group can be protected by a tert. butoxycarbonyl, benzyloxycarbonyl, formyl, trityl, trifluoroacetyl, 2-(biphenylyl)-isopropoxycarbonyl or isobornyloxycarbonyl group, or P and Q taken together are unsubstituted 1,2-phenylene, thienylene, 1,2-naphthylene, 2,3-naphthylene, 1,8-naphthylene or 2,3-anthrylene or substituted by one or more substituents selected from $C_1$–$C_6$-alkyl, $C_1$–$C_6$-alkoxy, halogen, hydroxy, phenyl-($C_1$–$C_6$-alkoxy) wherein phenyl is unsubstituted or substituted with one or more substituents selected from $C_1$–$C_6$-alkyl, $C_1$–$C_6$-alkoxy, halogen or trifluoromethyl, nitro, amino, $C_1$–$C_6$-alkanoylamino, mono($C_1$–$C_6$-alkyl)amino, di($C_1$–$C_6$-alkyl)amino or $C_1$–$C_6$-alkylsulfonylamino.

10. A compound according to claim 8, wherein X is a cyclic imido group of the formula

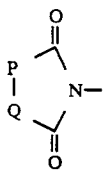
(b)

wherein P and Q taken together are a group of the formula

—CH(R$^f$)—CH(R$^f$)—,

—CH(R$^f$)—CH(R$^f$)—CH(R$^f$)—,

—O—CH($^f$)—,

—N(R$^f$)—CH(R$^f$)—,

—N(R$^f$)—N(R$^f$)—,

—N=N— or

—C(R$^f$)=C(R$^f$)— wherein each R$^f$ is a hydrogen; $C_1$-$C_6$-alkyl; phenyl unsubstituted or substituted with one or more substituents selected from $C_1$-$C_6$-alkyl, $C_1$-$C_6$-alkoxy, halogen or trifluoromethyl; phenyl -($C_1$-$C_6$-alkyl) wherein phenyl is unsubstituted or substituted with one or more substituents selected from $C_1$-$C_6$-alkyl, $C_1$-$C_6$-alkoxy, halogen or trifluoromethyl; $C_1$-$C_6$-alkanoylamino; or an acylamino group of the formula H$_2$N—CH(-R)—CONH— wherein R is isopropyl, isobutyl, benzyl, p-hydroxybenzyl, hydroxymethyl, mercaptomethyl, 1-hydroxyethyl, 2-methylthioethyl, carboxymethyl, 2-carboxyethyl, 3-quanidinopropyl or aminobutyl, in which the amino group can be protected by a tert. butoxycarbonyl, benzyloxycarbonyl, formyl, trityl, trifluoroacetyl, 2-(biphenylyl)-isopropoxycarbonyl or isobornyloxycarbonyl group, or P and Q taken together are unsubstituted 1,2-phenylene, thienylene, 1,2-naphthylene, 2,3-naphthylene, 1,8-naphthylene or 2,3-anthrylene or substituted by one or more substituents selected from $C_1$-$C_6$-alkyl, $C_1$-$C_6$-alkoxy, halogen, hydroxy, phenyl-($C_1$-$C_6$-alkoxy), nitro, amino, $C_1$-$C_6$-alkanoylamino, mono($C_1$-$C_6$-alkyl)amino, di($C_1$-$C_6$-alkyl)amino or $C_1$-$C_6$-alkylsulfonylamino.

11. A compound according to claim 9, where each R$^f$ is hydrogen, or a $C_1$-$C_6$-alkyl or $C_1$-$C_6$-alkanoylamino.

12. A compound according to claim 10, where P and Q taken together are a group of the formula —C(R$^f$)=C(R$^f$)— in which one R$^f$ is phenyl unsubstituted or substituted with one or more substituents selected from $C_1$-$C_6$-alkyl, $C_1$-$C_6$-alkoxy, halogen or trifluoromethyl and the other R$^f$ is hydrogen or phenyl unsubstituted or substituted with one or more substituents selected from $C_1$-$C_6$-alkyl, $C_1$-$C_6$-alkoxy, halogen or trifluoromethyl.

13. A compound according to claim 12, wherein one R$^f$ is phenyl and the other R$^f$ is hydrogen or phenyl.

14. A compound according to claim 10, wherein P and Q taken together are 1,2-phenylene or 2,3-naphthylene which is optionally substituted by one or more substituents selected from $C_1$-$C_6$-alkoxy, halogen, hydroxy, amino or $C_1$-$C_6$-alkanoylamino.

15. A compound according to claim 10, wherein P and Q taken together are 1,8-naphthylene which is optionally substituted by a $C_1$-$C_6$-alkoxy, hydroxy or amino.

16. A compound according to claim 11, wherein X is a cyclic imido group of the formula

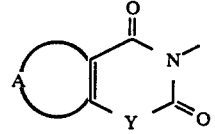
(c)

wherein A is the residue of benzene, naphthalene or anthracene which is unsubstituted or substituted by one or more substituents selected from $C_1$-$C_6$-alkyl, $C_1$-$C_6$-alkoxy, halogen, hydroxy, phenyl-($C_1$-$C_6$-alkoxy) wherein phenyl is unsubstituted or substituted with one or more substituents selected from $C_1$-$C_6$-alkyl, $C_1$-$C_6$-alkoxy, halogen or trifluoromethyl, nitro, amino, $C_1$-$C_6$-alkanoyl-amino, mono($C_1$-$C_6$-alkyl)amino, di($C_1$-$C_6$-alkyl)-amino and $C_1$-$C_6$-alkylsulfonylamino and Y is —O—, —NH— or —NR$^g$— in which R$^g$ is hydrogen or $C_1$-$C_6$-alkyl.

17. A compound according to claim 14, wherein A is the residue of a benzene ring and Y is —NR$^g$—.

18. A compound according to claim 15, wherein A is the residue of a benzene ring and Y is —NR$^g$—.

19. A compound according to claim 16, wherein X is a group of formula (a) in which R$^a$ is isopropyl, isobutyl, benzyl, p-hydroxybenzyl, hydroxymethyl, mercaptomethyl, 1-hydroxyethyl, 2-methylthioethyl, carboxymethyl, 2-carboxyethyl, 3-quanidinopropyl or aminobutyl, wherein a hydroxy group can be protected by a tert-butyl benzyl, tetrahydropyranyl or acetyl group, a mercapto group can be protected by a tert-butyl or benzyl group, an amino group can be acylated by a tert. butoxycarbonyl, benzyloxycarobnyl, formyl, trityl, trifluoroacetyl, 2-(biphenylyl)isopropoxycarbonyl or isobornyloxycarbonyl group, or can be sulfonylated by a $C_1$-$C_6$-alkanesulfonyl, benzenesulfonyl or p-toluenesulfonyl group, and a carboxyl group can be amidated to an aminocarbonyl, ($C_1$-$C_6$-alkyl)aminocarbonyl di($C_1$-$C_6$-alkyl)-aminocarbonyl or phenylaminocarbonyl and R$^b$ is hydrogen, R$^c$ and R$^d$ taken together are trimethylene and R$^e$ is a protecting group selected from tert. butoxycarbonyl, benzyloxycarbonyl, formyl, trityl, trifluoroacetyl, 2-(biphenylyl)-isopropoxy-carbonyl or isobornyloxycarbonyl, or acyl is derived from a $C_1$-$C_6$-alkanoic acid or a phenyl-($C_1$-$C_6$-alkanoic) acid wherein phenyl is unsubstituted or substituted with one or more substituents selected from $C_1$-$C_6$-alkyl, $C_1$-$C_6$-alkoxy, halogen or trifluoromethyl, $C_1$-$C_6$-alkylsulfonyl or phenylsulfonyl wherein phenyl is unsubstituted or substituted with one or more substituents selected from $C_1$-$C_6$-alkyl, $C_1$-$C_6$-alkoxy, halogen or trifluoromethyl.

20. A compound according to claim 17, wherein R$^a$ is isobutyl, R$^b$ is hydrogen, and R$^c$ and R$^d$ taken together are trimethylene.

21. A compound according to claim 20, wherein R$^e$ is benzyloxycarbonyl or acetyl.

22. A compound according to claim 1, [(3-Aminophthalimido)methyl][(RS)-4-methyl-2-[[(S)-3methyl-1- .

(methylcarbamoyl)butyl]carbamoyl]pentyl]phosphinic acid.

23. A compound according to claim 1, [(RS)-4-Methyl-2-[[(S)-3-methyl-1-(methylcarbamoyl)butyl]carbamoyl]pentyl](1,8-naphthalenedicarboximidomethyl)-phosphinic acid.

24. A compound according to claim 1, [(R or S)-4-Methyl-2-[[(R or S)-2-oxo-3-azacyclotridecyl]carbamoyl]pentyl]-(1,8-naphthalenedicarboximidomethyl)-phosphinic acid.

25. A compound according to claim 1, N-[N-[(R or S)-2[[[[[N-[1-(Benzyloxy)carbonyl]-L-leucyl]amino]methyl]hydroxyphosphinyl]methyl]-4-methylvaleryl]-L-leucyl]-L-alanine.

26. A compound according to claim 1, [[1,4-dihydro-2,4-dioxo-3(2H)-quinazolinyl]methyl]-[[(R or S)-4-methyl-2-[[(R or S)-2-oxo-3-azacyclotridecyl]carbamoyl]pentyl]phosphinic acid.

27. A pharmaceutical composition comprising an effective amount of a compound of the formula

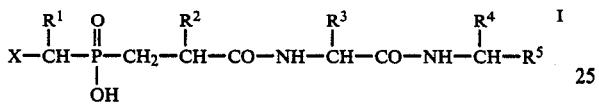

wherein $R^1$ is a hydrogen, $C_1-C$-alkyl or phenyl-($C_1-C_6$-alkyl) wherein phenyl is unsubstituted or substituted with one or more substituents selected from $C_1-C_6$-alkyl, $C_1-C_6$-alkoxy, halogen or trifluoromethyl;

$R^2$ is a $C_2-C_5$-alkyl;

$R^3$ is isopropyl, isobutyl, benzyl, p-hydroxybenzyl, hydroxymethyl, mercaptomethyl, 1-hydroxyethyl, 2-methylthioethyl, carboxymethyl, 2-carboxyethyl, 3-quanidinopropyl or aminobutyl, wherein a hydroxy group can be protected by a tert-butylbenzyl, tetrahydropyranyl or acetyl group, a mercapto group can be protected by a tert-butyl or benzyl group, an amino group can be acylated by a tert. butoxycarbonyl, benzyloxycarbonyl, formyl, trityl, trifluoroacetyl, 2-(biphenylyl)isopropoxycarbonyl or isobornyloxycarbonyl group, or can be sulfonylated by a $C_1-C_6$-alkane-sulfonyl, benzenesulfonyl or p-toluenesulfonyl group, and a carboxyl group can be amidated to an aminocarbonyl, ($C_1-C_6$-alkyl)aminocarbonyl, di($C_1-C_6$-alkyl)aminocarbonyl or phenylaminocarbonyl;

$R^4$ is a hydrogen or methyl; or $R^3$ and $R^4$ taken together are a group of the formula —$(CH_2)_n$— in which n is an integer from 4 to 11 inclusive;

$R^5$ is a hydrogen, $C_1-C_6$-alkyl, carboxyl, $C_1-C_6$-alkoxycarbonyl or $C_1-C_6$-alkylaminocarbonyl; and X is either a cyclic imido group of the formula

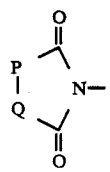

wherein

P and Q taken together are a group of the formula
—CH(R/)—CH(R/)—, —CH(R/)—CH(R/)—CH(R/)—, —O—CH(R/)—, —N(R/)—CH(R/)—, —N(R-/)—N(R/)—, —N=N— or —C(R/)=C(R/)— in which each R/ is a hydrogen; $C_1-C_6$-alkyl; phenyl unsubstituted or substituted with one or more substituents selected form $C_1-C_6$-alkyl, $C_1-C_6$-alkoxy, halogen or trifluoromethyl; phenyl-($C_1-C_6$-alkyl) wherein phenyl is unsubstituted or substituted with one or more substituents selected from $C_1-C_6$-alkyl, $C_1-C_6$-alkoxy, halogen or trifluoromethyl; $C_1-C_6$-alkanoylamino; or an acylamino group of the formula $H_2N$—CH(-R)—CONH— wherein R is isopropyl, isobutyl, benzyl, p-hydroxybenzyl, hydroxymethyl, mercaptomethyl, 1-hydroxyethyl, 2-methylthioethyl, carboxymethyl, 2-carboxyethyl, 3-quanidinopropyl or aminobutyl, in which the amino group can be protected by a tert. butoxycarbonyl, benzyloxycarbonyl, formyl, trityl, trifluoroacetyl, 2-(biphenylyl)-isopropoxycarbonyl or isobornyloxycarbonyl group, or P and Q taken together are unsubstituted 1,2-phenylene, thienylene, 1,2-naphthylene, 2,3-naphthylene, 1,8-naphthylene or 2,3-anthrylene or substituted by one or more substituents selected from $C_1-C_6$-alkyl, $C_1-C_6$-alkoxy, halogen, hydroxy, phenyl($C_1-C_6$-alkoxy) wherein phenyl is unsubstituted or substituted with one or more substituents selected from the $C_1-C_6$-alkyl, $C_1-C_6$-alkoxy, halogen or trifluoromethyl, nitro, amino, $C_1-C_6$-alkanoylamino, mono($C_1-C_6$-alkyl)amino, di($C_1-C_6$-alkyl)-amino and $C_1-C_6$-alkylsulfonylamino; or a group of the formula

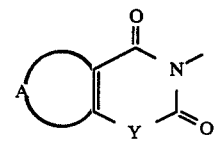

wherein

A is the residue of benzene, naphthalene or enthracene which is unsubstituted or substituted by one or more substituents selected from $C_1-C_6$-alkyl, $C_1-C_6$-alkoxy, halogen, hydroxy, phenyl-($C_1-C_6$-alkoxy) wherein phenyl is unsubstituted or substituted with one or more substituents selected from $C_1-C_6$-alkyl, $C_1-C_6$-alkoxy, halogen or trifluoromethyl, nitro, amino, $C_1-C_6$-alkanoyl-amino, mono($C_1-C_6$-alkyl)amino, di($C_1-C_6$-alkyl)-amino and $C_1-C_6$-alkylsulfonylamino and Y is —O—, —NH— or —NR$^q$ in which R$^q$ is hydrogen or $C_1-C_6$-alkyl, or a group of the formula

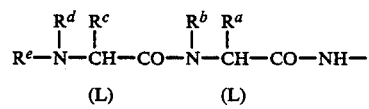

$R^a$ is isopropyl, isobutyl, benzyl, p-hydroxybenzyl, hydroxymethyl mercaptomethyl, 1-hydroxyethyl, 2-methylthioethyl, carboxymethyl, 2-carboxyethyl, 3-quanidinopropyl or aminobutyl, wherein a hydroxy group can be protected by a tert-butyl benzyl, tetrahydropyranyl or acetyl group, a mercapto group can be protected by a tert-butyl or benzyl group, an amino group can be acylated by a tert. butoxycarbonyl, benzyloxycarbonyl, formyl, trityl, trifluoroacetyl, 2-(biphenylyl)isopropoxycarbonyl or isobornyloxycarbonyl group, or can be sulfonylated by a $C_1-C_6$-alkane-sulfonyl, benzenesulfonyl or p- toluenesulfonyl group, and a carboxyl group can be amidated to an aminocarbonyl, ($C_1$–$C_6$-alkyl)aminocarbonyl, di($C_1$–$C_6$-alkyl)-amino-carbonyl or phenylaminocarbonyl, $R^b$ is hydrogen or $R^a$ and $R^b$ taken together are trimethylene, $R^c$ is isopropyl, isobutyl, benzyl, p-hydroxybenzyl, hydroxymethyl, mercaptomethyl, 1-hydroxyethyl, 2-methylthioethyl, carboxymethyl, 2-carboxyethyl, 3-quanidinopropyl or aminobutyl, wherein a hydroxy group can be protected by a tert-butyl benzyl, tetrahydropyranyl or acetyl group, a mercapto group can be protected by a tert-butyl or benzyl group, an amino group can be acylated by a tert. butoxycarbonyl, benzyloxycarbonyl, formyl, trityl, trifluoroacetyl, 2-(biphenylyl)isopropoxycarbonyl or isobornyloxycarbonyl group, or can be sulfonylated by a $C_1$–$C_6$-alkane-sulfonyl, benzenesulfonyl or p-toluenesulfonyl group, and a carboxyl group can be amidated to an aminocarbonyl, ($C_1$–$C_6$-alkyl)-aminocarbonyl, di($C_1$–$C_6$-alkyl)amino-carbonyl or phenylaminocarbonyl;

$R^d$ is hydrogen or $R^c$ and $R^d$ taken together are trimethylene and $R^e$ is a protecting group selected from tert. butoxycarbonyl, benzyloxycarbonyl, formyl, trityl, trifluoroacetyl, 2-(biphenylyl)-isopropoxycarbonyl or isobornyloxycarbonyl, acyl is derived from a $C_1$–$C_6$-alkanoic acid or a phenyl-($C_1$–$C_6$-alkanoic) acid wherein phenyl is unsubstituted or substituted with one or more substituents selected from $C_1$–$C_6$-alkyl, $C_1$–$C_6$-alkoxy, halogen or trifluoromethyl, $C_1$–$C_6$-alkyl-sulfonyl or phenylsulfonyl wherein phenyl is unsubstituted or substituted with one or more substituents selected from $C_1$–$C_6$-alkyl, $C_1$–$C_6$-alkoxy, halogen or trifluoromethyl, or a pharmaceutically acceptable salt thereof and an inert pharmaceutical carrier.

28. A pharmaceutical composition according to claim 27, wherein the compound of formula I is [(3-aminophthalimido)methyl][(RS)-4-methyl-2-[[(S)-3-methyl-1-(methylcarbamoyl)butyl]carbamoyl]pentyl]phosphinic acid.

29. A pharmaceutical composition according to claim 27, wherein the compound of formula I is [(RS)-4-methyl-2-[[(S)-3-methyl-1-(methylcarbamoyl)butyl]carbamoyl]pentyl]-(1,8-naphthalenedicarboximidomethyl)phosphinic acid.

30. A pharmaceutical composition according to claim 27, wherein the compound of formula I is [(R or S)-4-methyl-2-[[(R or S)-2-oxo-3-azacyclotridecyl]carbamoyl]pentyl](1,8-naphthalenedicarboximidomethyl)phosphinic acid.

31. A pharmaceutical composition according to claim 27, wherein the compound of formula I is N-[N-[(R or S)-2-[[[[[N-[1-(benzyloxy)carbonyl]-L-propyl]-L-leucyl]amino]methyl]hydroxyphosphinyl]methyl]-4-methylvaleryl]-L-leucyl]-L-alanine.

32. A pharmaceutical composition according to claim 27, wherein the compound of formula I is [[1,4-dihydro-2,4-dioxo-3(2H)-quinazolinyl]methyl]-[[(R or S)-4-methyl-2-[[(R or S)-2-oxo-3-azacyclotridecyl]carbamoyl]pentyl]phosphinic acid.

33. A method of controlling or preventing a degenerative joint disease which comprises administering to a host requiring such treatment an effective amount of a compound of the formula

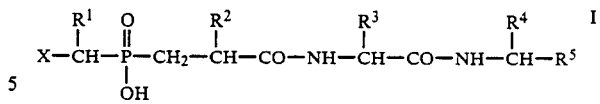

wherein $R^1$ is a hydrogen, $C_1$–$C_6$-alkyl or phenyl-($C_1$–$C_6$-alkyl) wherein phenyl is unsubstituted or substituted with one or more substituents selected from $C_1$–$C_6$-alkyl, $C_1$–$C_6$-alkoxy, halogen or trifluoromethyl;

$R^2$ is a $C_2$–$C_5$-alkyl;

$R^3$ is isopropyl, isobutyl, benzyl, p-hydroxybenzyl, hydroxymethyl, mercaptomethyl, 1-hydroxyethyl, 2-methylthioethyl, carboxymethyl, 2-carboxyethyl, 3-quanidinopropyl or aminobutyl, wherein a hydroxy group can be protected by a tert-butylbenzyl, tetrahydropyranyl or acetyl group, a mercapto group can be protected by a tert-butyl or benzyl group, an amino group can be acylated by a tert. butoxycarbonyl, benzyloxycarbonyl, formyl, trityl, trifluoroacetyl, 2-(biphenylyl)isopropoxycarbonyl or isobornyloxycarbonyl group, or can be sulfonylated by a $C_1$–$C_6$-alkane-sulfonyl, benzenesulfonyl or p-toluenesulfonyl group, and a carboxyl group can be amidated to an aminocarbonyl, ($C_1$–$C_6$-alkyl)aminocarbonyl, di($C_1$–$C_6$-alkyl)aminocarbonyl or phenylaminocarbonyl;

$R^4$ is a hydrogen or methyl; or $R^3$ and $R^4$ taken together are a group of the formula —(CH$_2$)$_n$— in which n is an integer from 4 to 11 inclusive;

$R^5$ is a hydrogen, $C_1$–$C_6$-alkyl, carbonyl, $C_1$–$C_6$-alkoxycarbonyl or $C_1$–$C_6$-alkylaminocarbonyl; and X is either a cyclic imido group of the formula

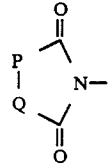 (b)

wherein

P and Q taken together are a group of the formula —CH(R$^f$)—CH(R$^f$)—, —CH(R$^f$)=CH(R$^f$)—CH(R$^f$)—, —O—CH(R$^f$)—, —N(R$^f$)—CH(R$^f$)—, —N(R$^f$)—N(R$^f$)—, —N=N— or —C(R$^f$)=C(R$^f$)— in which each is a hydrogen; $C_1$–$C_6$-alkyl; phenyl unsubstituted or substituted with one or more substituents selected form $C_1$–$C_6$-alkyl, $C_1$–$C_6$-alkoxy, halogen or trifluoromethyl; phenyl-($C_1$–$C_6$-alkyl) wherein phenyl is unsubstituted or substituted with one or more substituents selected from $C_1$–$C_6$-alkyl, $C_1$–$C_6$-alkoxy, halogen or trifluoromethyl; $C_1$–$C_6$-alkanoylamino; or an acylamino group of the formula H$_2$N—CH(R)—CONH— wherein R is isopropyl, isobutyl, benzyl, p-hydroxybenzyl, hydroxymethyl, mercaptomethyl, 1-hydroxyethyl, 2-methylthioethyl, carboxymethyl, 2-carboxyethyl, 3-quanidinopropyl or aminobutyl, in which the amino group can be protected by a tert. butoxycarbonyl, benzyloxycarbonyl, formyl, trityl, trifluoroacetyl, 2-(biphenylyl)-isopropoxycarbonyl or isobornyloxycarbonyl group, or P and Q taken together are unsubstituted 1,2-phenylene, thienylene, 1,2-naphthylene, 2,3-naphthylene, 1,8-naphthylene or 2,3-anthrylene or substituted by one or more substituents selected from $C_1$–$C_6$-alkyl, $C_1$–$C_6$-alkoxy, halogen, hydroxy, phenyl($C_1$–$C_6$-alkoxy) wherein phenyl is unsubstituted or substituted with one or more substituents selected from $C_1$–$C_6$-alkyl, $C_1$–$C_6$-alkoxy, halogen or trifluoromethyl, nitro, amino, $C_1$–$C_6$-alkanoylamino, mono($C_1$–$C_6$-alkyl)amino, di($C_1$–$C_6$-alkyl)-amino and $C_1$–$C_6$-alkylsulfonylamino; or a group of the formula

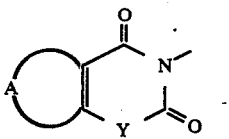 (c)

wherein

A is the residue of benzene, naphthalene or enthracene which is unsubstituted or substituted by one or more substituents selected from $C_1$–$C_6$-alkyl, $C_1$–$C_6$-alkoxy, halogen, hydroxy, phenyl-($C_1$–$C_6$-alkoxy) wherein phenyl is unsubstituted or substituted with one or more substituents selected from $C_1$–$C_6$-alkyl, $C_1$–$C_6$-alkoxy, halogen or trifluoromethyl, nitro, amino, $C_1$–$C_6$-alkanoyl-amino, mono($C_1$–$C_6$-alkyl)amino, di($C_1$–$C_6$-alkyl)-amino and $C_1$–$C_6$-alkylsulfonylamino and Y is —O—, —NH— or —NR$^q$ in which R$^q$ is hydrogen or $C_1$–$C_6$-alkyl, or a group of the formula

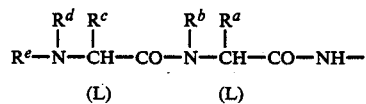 (a)

$R^a$ is isopropyl, isobutyl, benzyl, p-hydroxybenzyl, hydroxymethyl, mercaptomethyl, 2-hydroxyethyl, 2-methylthioethyl, carboxymethyl, 2-carboxyethyl, 3-quanidinopropyl or aminobutyl, wherein a hydroxy group can be protected by a tert-butyl benzyl, tetrahydropyranyl or acetyl group, a mercapto group can be protected by a tert-butyl or benzyl group, an amino group can be acylated by a tert. butoxycarbonyl, benzyloxycarbonyl, formyl, trityl, trifluoroacetyl, 2-(biphenylyl)isopropoxycarbonyl or isobornyloxycarbonyl group, or can be sulfonylated by a $C_1$–$C_6$-alkane-sulfonyl, benzenesulfonyl or p-toluenesulfonyl group, and a carboxyl group can be amidated to an aminocarbonyl, ($C_1$–$C_6$-alkyl)aminocarbonyl, di($C_1$–$C_6$-alkyl)-aminocarbonyl or phenylaminocarbonyl, $R^b$ is hydrogen or $R^a$ and $R^b$ taken together are trimethylene, $R^c$ is isopropyl, isobutyl, benzyl, p-hydroxybenzyl, hydroxymethyl, mercaptomethyl, 1-hydroxyethyl, 2-methylthioethyl, carboxymethyl, 2-carboxyethyl, 3-quanidinopropyl or aminobutyl, wherein a hydroxy group can be protected by a tert-butyl benzyl, tetrahydropyranyl or acetyl group, a mercapto group can be protected by a tert-butyl or benzyl group, an amino group can be acylated by a tert. butoxycarbonyl, benzyloxycarbonyl, formyl, trityl, trifluoroacetyl, 2-(biphenylyl)isopropoxycarbonyl or isobornyloxycarbonyl group, or can be sulfonylated by a $C_1$–$C_6$-alkanesulfonyl, benzenesulfonyl or p-toluenesulfonyl group, and a carboxyl group can be amidated to an aminocarbonyl, ($C_1$–$C_6$-alkyl)-aminocarbonyl, di($C_1$–$C_6$-alkyl)-aminocarbonyl or phenylaminocarbonyl, $R^d$ is hydrogen or $R^c$ and $R^d$ taken together are trimethylene and $R^e$ is a protecting group selected from tert. butoxycarbonyl, benzyloxycarbonyl, formyl, trityl, trifluoroacetyl, 2-(biphenylyl)-isopropoxycarbonyl or isobornyloxycarbonyl, acyl is derived from a $C_1$–$C_6$-alkanoic acid or a phenyl-($C_1$–$C_6$-alkanoic) acid wherein phenyl is unsubstituted or substituted with one or more substituents selected from $C_1$–$C_6$-alkyl, $C_1$–$C_6$-alkoxy, halogen or trifluoromethyl, $C_1$–$C_6$-alkyl-sulfonyl or phenylsulfonyl wherein phenyl is unsubstituted or substituted with one or more substituents selected from $C_1$–$C_6$-alkyl, $C_1$–$C_6$-alkoxy, halogen or trifluoromethyl, or a pharmaceutically acceptable salt thereof.

34. A method according to claim 33, wherein the compound of formula I is [(3-aminophthalimido)methyl]-[(RS)-4-methyl-2-[[(S)-3-methyl-1-(methylcarbamoyl)butyl]carbamoyl]pentyl] phosphinic acid.

35. A method according to claim 33, wherein the compound of formula I is [(RS)-4-methyl-2-[[(S)-3-methyl-1-(methylcarbamoyl)butyl]carbamoyl]pentyl](1,8-naphthalenedicarboximidomethyl)phosphinic acid.

36. A method according to claim 33, wherein the compound of formula I is [(R or S)-4-methyl-2-[[(R or S)-2-oxo-3-azacyclotridecyl]carbamoyl]pentyl](1,8-naphthalenedicarboximidomethyl)phosphinic acid.

37. A method according to claim 33, where in the compound of formula I is N-[N-[(R or S)-2-[[[[[N-[1-(benzyloxy)carbonyl]-L-prolyl]-L-leucyl]amino]methyl]-hydroxyphosphinyl]methyl]-4-methylvaleryl]-L-leucyl]-L-alanine.

38. A method according to claim 33, wherein the compound of formula I is [[1,4-dihydro-2,4-dioxo-3(2H)-quinazolinyl]methyl]-[[(R or S)-4-methyl-2-[[(R or S)-2-oxo-3-azacyclotridecyl]carbamoyl]pentyl]phosphinic acid.

* * * * *

UNITED STATES PATENT AND TRADEMARK OFFICE
CERTIFICATE OF CORRECTION

PATENT NO. : 4,885,283

DATED : December 5, 1989

INVENTOR(S) : Michael John Broadhurst et al

It is certified that error appears in the above-identified patent and that said Letters Patent is hereby corrected as shown below:

In claim 25, line 2 after "carbonyl] " insert
--- -L-prolyl] ---

In claim 33, column 52, line 50, after "each" insert
---$R^f$---

In claim 33, column 53, line 37, "2" should be replaced with ---1---

Signed and Sealed this

Fifth Day of March, 1991

Attest:

HARRY F. MANBECK, JR.

Attesting Officer

Commissioner of Patents and Trademarks